(12) United States Patent
Ichiki et al.

(10) Patent No.: US 10,775,368 B2
(45) Date of Patent: *Sep. 15, 2020

(54) FLUIDIC DEVICE, SYSTEM, AND METHOD

(71) Applicants: The University of Tokyo, Bunkyo-ku, Tokyo (JP); NIKON CORPORATION, Minato-ku, Tokyo (JP)

(72) Inventors: Takanori Ichiki, Tokyo (JP); Taro Ueno, Tokyo (JP); Ryo Kobayashi, Kawasaki (JP); Hirofumi Shiono, Fujisawa (JP)

(73) Assignees: The University of Tokyo, Tokyo (JP); NIKON CORPORATION, Tokyo (JP)

( * ) Notice: Subject to any disclaimer, the term of this patent is extended or adjusted under 35 U.S.C. 154(b) by 20 days.

This patent is subject to a terminal disclaimer.

(21) Appl. No.: 15/679,816

(22) Filed: Aug. 17, 2017

(65) Prior Publication Data

US 2017/0370922 A1      Dec. 28, 2017

Related U.S. Application Data

(63) Continuation of application No. PCT/JP2016/059477, filed on Mar. 24, 2016.

(30) Foreign Application Priority Data

Mar. 24, 2015  (JP) ................................ 2015-061803

(51) Int. Cl.
*G01N 33/543* (2006.01)
*B01F 5/10* (2006.01)
(Continued)

(52) U.S. Cl.
CPC ....... *G01N 33/54326* (2013.01); *B01F 5/102* (2013.01); *B01F 13/0059* (2013.01);
(Continued)

(58) Field of Classification Search
None
See application file for complete search history.

(56) References Cited

U.S. PATENT DOCUMENTS 6,408,884 B1    6/2002  Kamholz et al.
2005/0148064 A1  7/2005  Yamakawa et al.
(Continued)

FOREIGN PATENT DOCUMENTS

EP      3051293 A1    8/2016
WO    WO 01/94635 A2  12/2001

OTHER PUBLICATIONS

Hong et al., "A nanoliter-scale nucleic acid processor with parallel architecture", Nature Biotechnology. Apr. 2004; 22(4): 435-439.
(Continued)

*Primary Examiner* — Changhwa J Cheu
(74) *Attorney, Agent, or Firm* — Squire Patton Boggs (US) LLP

(57) ABSTRACT

A fluidic device includes: a circulation flow path; and a capture part arranged on the circulation flow path and configured to capture a sample substance in a solution and/or a detection part arranged on the circulation flow path and configured to detect a sample substance in a solution. A method of capturing a sample substance that is bound to a carrier particle, using a fluidic device which includes a circulation flow path and a capture part arranged on the circulation flow path and configured to capture the carrier particle and in which the circulation flow path has two or more circulation flow path valves, includes: an introduction step of, in a state where the circulation flow path valve is closed, introducing a solution that includes a sample substance to at least one of partitions partitioned by the circulation flow path valve and introducing a solution that includes a carrier particle which is bound to the sample substance to at least another of the partitions; a mix step of
(Continued)

opening all of the circulation flow path valves and circulating and mixing a solution in the circulation flow path; and a capture step of capturing the carrier particle by the capture part.

13 Claims, 16 Drawing Sheets

(51) Int. Cl.
    *B01F 13/00* (2006.01)
    *B01L 3/00* (2006.01)
    *C12Q 1/6834* (2018.01)

(52) U.S. Cl.
    CPC ..... *B01L 3/50273* (2013.01); *B01L 3/502738* (2013.01); *B01L 3/502761* (2013.01); *C12Q 1/6834* (2013.01); *B01L 2200/0668* (2013.01); *B01L 2300/0627* (2013.01); *B01L 2300/088* (2013.01); *B01L 2300/0816* (2013.01); *B01L 2300/0867* (2013.01); *B01L 2400/0481* (2013.01); *B01L 2400/06* (2013.01); *B01L 2400/0605* (2013.01); *C12Q 2565/631* (2013.01)

(56) References Cited

U.S. PATENT DOCUMENTS

| | | | |
|---|---|---|---|
| 2012/0270331 A1* | 10/2012 | Achrol | B01L 3/502761 436/177 |
| 2013/0260481 A1 | 10/2013 | Shimizu et al. | |
| 2013/0295653 A1* | 11/2013 | Quake | B01F 5/0646 435/283.1 |

OTHER PUBLICATIONS

International Search Report and Written Opinion dated Jun. 21, 2016, in International Patent Application No. PCT/JP2016/059477, 16 pages.

EPO Communication dated Jul. 31, 2018 issued for European Patent Application No. 16768909.0, 7 pages.

* cited by examiner

| | BEFORE TRANSPORT | DURING TRANSPORT | AFTER TRANSPORT |
|---|---|---|---|
| WITHOUT MAGNET | | | |
| WITH MAGNET | | | |

FLUIDIC DEVICE, SYSTEM, AND METHOD

CROSS-REFERENCE TO RELATED APPLICATION

This is a Continuation Application of International Application No. PCT/JP2016/059477, filed on Mar. 24, 2016, which claims priority on Japanese Patent Application No. 2015-61803, filed on Mar. 24, 2015. The contents of the aforementioned applications are incorporated herein by reference.

BACKGROUND

Field of the Invention

The present invention relates to a circulation mixer, a fluidic device, a system, and a method.

Background

In recent years, developments of micro-total analysis systems (μ-TAS) which aim at increasing speed, increasing efficiency, and integration of testing in the in vitro diagnostic field or ultra-miniaturization of a testing device have attracted attention, and active research has been globally conducted.

The μ-TAS are excellent in that measurement or analysis can be made using a small amount of samples, portability is realized, disposability at low cost is realized, and the like compared to testing devices of the related art.

Further, the μ-TAS have attracted attention as a method having high usefulness in a case of using an expensive reagent or in a case of testing a small amount of multiple specimens.

A rotary mixer that includes a loop-like flow path and a pump which is arranged on the flow path has been reported as a constituent of the μ-TAS (Jong Wook Hong, Vincent Studer, Giao Hang, W French Anderson and Stephen R Quake, Nature Biotechnology 22, 435-439 (2004)). In this rotary mixer, a plurality of solutions are injected into the loop-like flow path, and the pump is operated to thereby mix the plurality of solutions together in the loop-like flow path. The plurality of solutions are loaded in an injection flow path which is connected to the loop-like flow path and are then injected into the loop-like flow path. Valves are provided on the injection flow path, and the volume of each of the solutions is quantitatively determined within the flow path.

SUMMARY

In the in vitro diagnostic field, specifically in the point of care testing (POCT), it is necessary to perform a plurality of reactions continuously in a short time using a small amount of samples. However, according to the method described in Jong Wook Hong, Vincent Studer, Giao Hang, W French Anderson and Stephen R Quake, Nature Biotechnology 22, 435-439 (2004), the loop-like flow path is used for only circulating liquid, then a solution is transported to the outside of the loop to detect a DNA, and the method does not sufficiently satisfy such needs.

An aspect of the present invention provides the following (1) to (6).

(1) A fluidic device in an aspect of the present invention includes
a circulation flow path, and
a capture part arranged on the circulation flow path and configured to capture a sample substance in a solution and/or a detection part arranged on the circulation flow path and configured to detect a sample substance in a solution.

(2) A fluidic device in an aspect of the present invention includes a first circulation flow path, a second circulation flow path, and a connection flow path that directly or indirectly connects the first circulation flow path and the second circulation flow path, wherein
a capture part configured to capture a sample substance in a solution is arranged on the first circulation flow path, and
a detection part configured to detect a sample substance in a solution is arranged on the second circulation flow path.

(3) A system in an aspect of the present invention includes a fluidic device and a control part configured to control opening and closing of a valve.

(4) A method in an aspect of the present invention is
a method of capturing a sample substance that is bound to a carrier particle
using a fluidic device which includes a circulation flow path and a capture part arranged on the circulation flow path and configured to capture the carrier particle and in which the circulation flow path has two or more circulation flow path valves, the method including
an introduction step of, in a state where the circulation flow path valve is closed, introducing a solution that includes a sample substance to at least one of partitions partitioned by the circulation flow path valve and introducing a solution that includes a carrier particle which is bound to the sample substance to at least another of the partitions,
a mix step of opening all of the circulation flow path valves and circulating and mixing a solution in the circulation flow path, and
a capture step of capturing the carrier particle by the capture part.

(5) A method in an aspect of the present invention is
a method of detecting a sample substance that is bound to a carrier particle
using a fluidic device which includes a circulation flow path, a capture part arranged on the circulation flow path and configured to capture the carrier particle, and a detection part arranged on the circulation flow path and configured to detect a sample substance that is bound to a carrier particle captured by the capture part and in which the circulation flow path has two or more circulation flow path valves, the method including
an introduction step of, in a state where the circulation flow path valve is closed, introducing a solution that includes a sample substance to at least one of partitions partitioned by the circulation flow path valve and introducing a solution that includes a carrier particle which is bound to the sample substance to at least another of the partitions,
a mix step of opening all of the circulation flow path valves and circulating and mixing a solution in the circulation flow path,
a capture step of capturing the carrier particle by the capture part, and
a detection step of detecting, by the detection part, a sample substance that is bound to the carrier particle captured by the capture part.

(6) A method in an aspect of the present invention is
a method of detecting a sample substance that is bound to a carrier particle
using a fluidic device that includes a first circulation flow path having two or more circulation flow path valves, a second circulation flow path, and a connection flow path that directly or indirectly connects the first circulation flow path and the second circulation flow path, wherein
a capture part configured to capture a carrier particle is arranged on the first circulation flow path, and
a detection part configured to detect a sample substance that is bound to the carrier particle is arranged on the second circulation flow path, the method including
an introduction step of, in a state where a circulation flow path valve of the first circulation flow path is closed, introducing a solution that includes a sample substance to at least one of partitions partitioned by the first circulation flow path valve and introducing a solution that includes a carrier particle which is bound to the sample substance to at least another of the partitions,
a mix step of opening all of the circulation flow path valves of the first circulation flow path and circulating and mixing a solution in the first circulation flow path,
a capture step of capturing the carrier particle by the capture part,
a transport step of releasing the carrier particle from the capture part or releasing the sample substance from the carrier particle and transporting a solution that includes the released sample substance or the sample substance which is bound to the carrier particle to the second circulation flow path via the connection flow path, and
a detection step of detecting the sample substance by the detection part.

DESCRIPTION OF EMBODIMENTS

Hereinafter, embodiments of a circulation mixer, a fluidic device, a system, a mix method, a capture method, and a detection method will be described with reference to the drawings.

First Embodiment of Fluidic Device

A fluidic device of a first embodiment has a circulation mixer of a first embodiment. The fluidic device is a substrate in which a flow path inside which a sample solution moves is formed. A configuration included in the circulation mixer is included also in the fluidic device.

First, the first embodiment of the circulation mixer is described.

Figure 1:
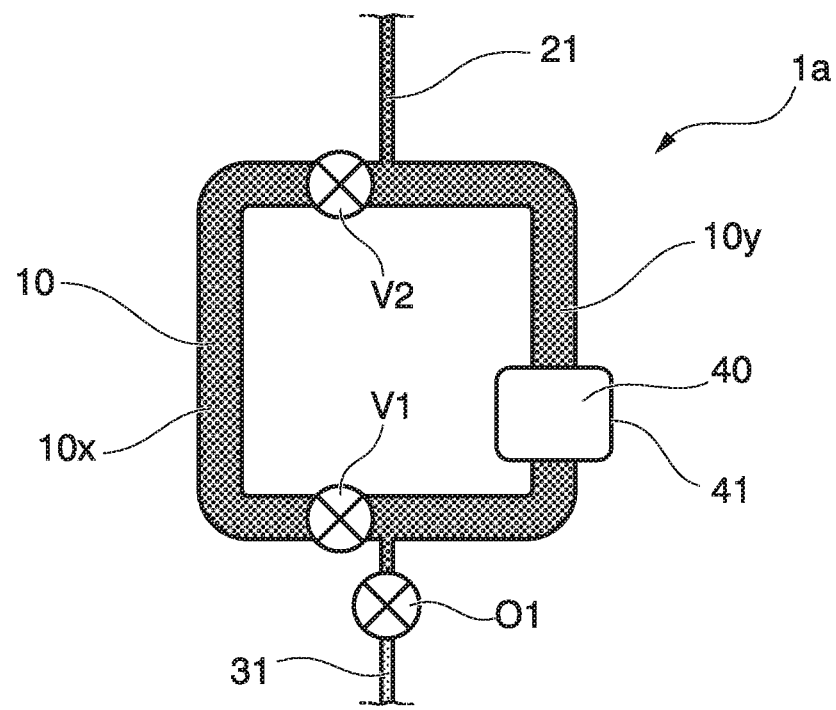
FIG. 1 is a plan view showing a schematic configuration of a fluidic device according to an embodiment of the present invention.

FIG. 1 is a plan view showing the circulation mixer of the first embodiment. The circulation mixer 1a includes a circulation flow path 10. The circulation flow path is a flow path capable of repeatedly circulating at least part of a solution. At least one introduction flow path and at least one discharge flow path may be connected to the circulation flow path. A discharge flow path 31 and an introduction flow path 21 are connected to the circulation flow path 10 included in the circulation mixer 1a of the first embodiment. Liquid is discharged from the circulation flow path 10 via the discharge flow path 31, and liquid is introduced to the circulation flow path 10 via the introduction flow path 21. The discharge flow path 31 may include a discharge flow path valve O1.

The circulation mixer 1a of the first embodiment includes the circulation flow path 10, the introduction flow path 21, the discharge flow path 31, the discharge flow path valve O1, a first circulation flow path valve V1, a second circulation flow path valve V2, and a capture part 40.

In the circulation mixer 1a, it is possible to control discharging and filling of liquid, air, and the like in the circulation flow path 10 by operating opening and closing of the first circulation flow path valve V1, the second circulation flow path valve V2, and the discharge flow path valve O1. In the first circulation flow path 10 of the present embodiment, due to interaction (friction) between a solution and a wall surface in the flow path, the flow rate in the vicinity of the wall surface is slow, and the flow rate in the middle of the flow path is fast. As a result, distribution of the flow rate of the liquid occurs, and therefore, mixing of the solution is prompted. The circulation flow path 10 may have a sharp curve or a flow path having an S shape or a zigzag shape in order to prompt stirring of the liquid. The inner diameter of the flow path is 0.01 mm to 3 mm as an example and is, for example, 0.5 mm to 1.5 mm.

The circulation flow path may have two or more circulation flow path valves. As an example, the circulation flow path 10 in FIG. 1 has two valves; namely, the first circulation flow path valve V1 and the second circulation valve V2. At least one of the introduction flow path and the discharge flow path is arranged in the vicinity of the circulation flow path valve. For example, in FIG. 1, the introduction flow path 21 is arranged in the vicinity of the second circulation flow path valve V2, and the discharge flow path 31 is arranged in the vicinity of the first circulation flow path valve V1.

The first circulation flow path valve V1 and the second circulation flow path valve V2 partition the circulation flow path 10. In FIG. 1, the first circulation flow path valve V1 is arranged on the left side in the vicinity of the discharge flow path 31 in the circulation flow path 10, and the second circulation flow path valve V2 is arranged on the left side in the vicinity of the introduction flow path 21 in the circulation flow path 10. In a case where the circulation flow path valve is away from the introduction flow path or the discharge flow path, when liquid is introduced from the introduction flow path 21 in a state where the first circulation flow path valve V1 and the second circulation flow path valve V2 are closed, liquid or air that has been present before may remain between the circulation flow path valve and the introduction flow path or the discharge flow path. The term "vicinity" means, for example, a close distance in which such remaining of liquid or air does not occur.

In FIG. 1, the first circulation flow path valve V1 may be arranged on any of the right side and the left side of the discharge flow path 31, and the second circulation flow path valve V2 may be arranged on any of the right side and the left side of the introduction flow path 21. For example, in the circulation flow path 10, the first circulation flow path valve V1, an introduction flow path connection part, a discharge flow path connection part, and the second circulation flow path valve V2 may be arranged in this order in the clockwise direction. Alternatively, in the circulation flow path 10, the introduction flow path connection part, the first circulation flow path valve V1, the second circulation flow path valve V2, and the discharge flow path connection part may be arranged in this order in the clockwise direction.

The circulation flow path valves V1, V2 are arranged such that each of the partitions of the circulation flow path compartmentalized by the circulation flow path valves V1, V2 has a predetermined volume.

When the first circulation flow path valve V1 and the second circulation flow path valve V2 are closed, the circulation flow path 10 is partitioned into flow paths $10x$, $10y$ each having a predetermined volume. The flow path $10x$ of the circulation flow path 10 is a flow path that does not include the connection part to the discharge flow path 31 and the connection part to the introduction flow path 21. The flow path $10y$ of the circulation flow path 10 is a flow path that includes both of the connection part to the discharge flow path 31 and the connection part to the introduction flow path 21. By sending liquid from the introduction flow path 21 into the first circulation flow path 10 in a state where the first circulation flow path valve V1, the second circulation flow path valve V2, and the discharge flow path valve O1 are open and closing the first circulation flow path valve V1 and the second circulation flow path valve V2, it is possible to accommodate a predetermined volume of liquid in the flow path $10x$.

On the other hand, when the first circulation flow path valve V1 and the second circulation flow path valve V2 are opened, the partitioned circulation flow paths 10 come into communication with each other, and it is possible to mix the liquids held in each of the partitioned circulation flow paths.

The volume inside the circulation flow path 10 is determined in advance, and therefore, it is possible to mix the liquids in the circulation flow path 10 in a state where the volume of the liquid filled in the flow path $10x$ and the flow path $10y$ partitioned by the first circulation flow path valve V1 and the second circulation flow path valve V2 is accurately known.

The circulation flow path 10 may have a pump by which a solution is circulated. When the circulation flow path 10 includes a pump, the solution is sent according to a pump driving, and a plurality of solutions are easily mixed in the circulation flow path 10. Convection occurs according to the pump driving, and mixing of the plurality of solutions is prompted. The pump may be a pump valve capable of sending liquid by opening and closing of a valve. The pump may include at least three pump valves arranged on the circulation flow path 10. For example, when the circulation flow path 10 includes at least three pump valves, by controlling opening and closing of at least three valves, it is possible to control the direction in which the liquid is sent in the circulation flow path. The number of pump valves may be four or more. The pump is arranged in the circulation flow path 10, and thereby, further effective liquid circulation is realized. Further, the speed or direction of sending liquid can be controlled according to the driving of the pump. Any or all of the circulation flow path valves may be used as a pump valve. For example, at least one of the circulation flow path valves V1, V2 may be used as the pump valve. When the circulation flow path valve also has a function as the pump valve, it is possible to reduce the number of valves. Therefore, it is possible to reduce the number of drive systems for driving a valve.

The capture part 40 is arranged on the circulation flow path 10 and can capture a sample substance in a solution that is circulated in the circulation flow path 10. The capture part may capture a sample substance that is bound to a carrier particle. Hereinafter, a case is described in which a sample substance is bound to a carrier particle.

The capture part 40 that captures a carrier particle is provided on the circulation flow path 10.

The carrier particle is, as an example, a particle capable of reacting with a sample substance to be detected. The sample substance is, for example, a biomolecule such as a nucleic acid, a DNA, a RNA, a peptide, a protein, and an extracellular vesicle.

Examples of the reaction between a carrier particle and a sample substance include binding between the carrier particle and the sample substance, adsorption between the carrier particle and the sample substance, modification of the carrier particle by the sample substance, and chemical change of the carrier particle by the sample substance.

The carrier particle used in the present embodiment is not specifically limited as long as the carrier particle is a particle that is capable of reacting with a sample substance and being captured by the capture part 40, and examples of the carrier particle include magnetic beads, magnetic particles, gold nanoparticles, agarose beads, and plastic beads.

A carrier particle that includes, on the surface, a substance capable of being bound to or adsorbed by the sample substance may be used. For example, when binding a carrier particle and a predetermined protein, a carrier particle that includes, on the surface, an antibody capable of being bound to the protein can be used. The substance capable of being bound to the sample substance may be arbitrarily selected in accordance with the type of the sample substance. Examples of combination of a substance capable of being bound to or adsorbed by a sample substance/the sample substance or a region included in the sample substance include biotin-binding protein such as avidin and streptavidin/biotin, an active ester group such as a succinimidyl group/amino group, an iodinated acetyl group/amino group, a maleimide group/thiol group (—SH), maltose-binding protein/maltose, G protein/guanine nucleotide, polyhistidine peptide/metal ion such as nickel or cobalt, glutathione-S-transferase/glutathione, DNA-binding protein/DNA, antibody/antigen molecule (epitope), calmodulin/calmodulin-binding peptide, ATP-binding protein/ATP, or a variety of receptor proteins/ligands thereof such as estradiol receptor protein/estradiol.

The carrier particle and the sample substance may react in the circulation flow path 10. For example, by introducing the liquid that includes the carrier particle and the solution that includes the sample substance into the circulation flow path 10 to be mixed in the circulation flow path, a complex in which the carrier particle and the sample substance are bound to each other is formed. For example, when a biomolecule is fixed to a particle surface, and a sample substance that is bound to the biomolecule of the particle surface is present in the liquid, it is possible to increase a collision frequency by mixing and enhance a binding reaction rate between the biomolecule and the sample substance. For example, this technology is suitable for immunoassay in which the measurement of a single item is the mainstream.

Alternatively, the carrier particle and the sample substance may be reacted in advance, and an obtained complex may be introduced to the circulation flow path 10 and may be captured in the capture part 40.

The liquid that includes the carrier particle is circulated in the circulation flow path 10. The solution that includes the carrier particle flows in one direction or both directions in the circulation flow path and is circulated or reciprocated in the circulation flow path. The capture part 40 is provided on the circulation flow path 10. For example, a capture means that captures the carrier particle can be provided on the capture part 40. The capture part 40 can capture and collect a carrier particle from dispersion liquid of the carrier particle that is circulated in the circulation flow path 10. The capture means is not specifically limited as long as the capture means can capture the carrier particle. As an example, when a magnetic bead or a magnetic particle is used for the carrier particle, a magnetic force generation source such as a magnet can be used as the capture means. Alternatively, examples of the capture means include a column having a filling material capable of being bound to the carrier particle and an electrode capable of attracting the carrier particle.

The capture means may be provided on the capture part or the fluidic device described below to be integrated or may be separately provided outside the capture part or the fluidic device. The capture means may be removable from the capture part or the fluidic device.

The capture means and the carrier particle may be in direct contact with each other. The capture means and the carrier particle may not be in direct contact with each other as represented by the capture by a magnetic force as long as the capture part can capture the carrier particle. For example, as the capture means, a magnet may be arranged in the vicinity of a flow path outside a flow path of the circulation flow path 10.

The capture part 40 may be part of the circulation flow path 10. The entire circulation flow path 10 may have a capture means arrangement part. The size of the capture part 40 may be any size. The width of the capture part 40 may be wider than the width of the circulation flow path 10.

The capture part 40 may have a magnet arrangement part 41 at which a magnet can be arranged. It is preferable that the inner diameter inside the flow path in a direction orthogonally crossed with the magnet arrangement part 41 in the capture part 40 be formed to be smaller than the inner diameter inside the flow path in the direction orthogonally crossed with the magnet arrangement part 41 in the circulation flow path 10. Thereby, for example, when the capture means is a magnet, the distance from the capture means to the carrier particle inside the flow path becomes short, and the capture efficiency of the carrier particle is improved.

The capture part 40 may be configured such that the affinity with respect to the carrier particle is controllable. For example, by configuring such that the magnetic force of the magnet of the magnet arrangement part 41 is controllable, it is possible to control the capture and release (non-capture) of the carrier particle.

For example, by changing the distance between the magnet and the circulation flow path, the magnetic force given to the carrier particle may be controlled. By arranging the magnet on the magnet arrangement part 41 and arranging the magnet at a position close to the circulation flow path, the carrier particle is captured in the vicinity of the magnet arrangement part 41 in the circulation flow path 10 by the magnetic force. On the other hand, by removing the magnet from the magnet arrangement part 41 and allowing the magnet to be in a state away from the circulation flow path, the capture of the carrier particle captured by the inner wall surface of the circulation flow path 10 is released. The carrier particle becomes a free state from the capture state, and thereby, the carrier particle may be dispersed again in the solution.

When an electromagnet is used as the magnet, the strength of the magnetic force can be controlled by the control of the ON/OFF of the current and the current value.

At this time, it is possible to capture the carrier particle in a state where the carrier particle is bound to the sample substance. For example, by capturing the carrier particle that is bound to the sample substance to the capture part 40, it is possible to separate the sample substance and the carrier particle from the liquid that is circulated in the circulation flow path 10. Therefore, it is possible to effectively realize condensation, cleaning, and transport of the sample substance and the carrier particle.

The capture part 40 may have an array form capable of arraying the carrier particle. Examples of such a configuration include a configuration in which areas capable of capturing a carrier particle are arranged in an array form and a configuration in which holes capable of accommodating a carrier particle are arranged in an array form. For example, the area capable of capturing the carrier particle may have a well shape, and the size of the well may be 1 to 2 times larger than the diameter of the carrier particle such that the carrier particle enters the well one by one. The capture means may be a magnet array in which a plurality of magnets are arrayed in an array form. The sample substance that is bound to the carrier particle may be analyzed in a state where the capture part 40 captures the carrier particle. The carrier particle is captured in an array form, and thereby, the sample substance that is bound to the carrier particle is efficiently analyzed.

According to the circulation mixer of the first embodiment, since the first circulation flow path valve V1 and the second circulation flow path valve V2 are provided on the circulation flow path 10, in the mixer, volumes of a plurality of liquids are quantitatively determined accurately, and the plurality of liquids can be mixed. Since the circulation flow path 10 can be used for not only quantitative determination but also mixing, injection and quantitative determination of a solution to the circulation mixer 1a can be performed at the same time, and the operation can be made efficient.

Further, since the capture part 40 is provided on the circulation flow path 10, the liquid that includes the sample substance is caused to flow in one direction or both directions and is circulated or reciprocated in the circulation flow path, and the sample substance can be captured by the capture part. As the liquid that includes the sample substance can be circulated, the capture chance to the capture part 40 is prompted, and it is possible to capture the sample substance with high efficiency. By circulating the sample substance in the loop flow path, the sample substance passes through the capture area many times, and the capture efficiency is improved according to the integration effect. The sample substance may be bound to the carrier particle, and the carrier particle may be captured by the capture part 40. It is possible to perform cleaning or solution exchange while fixing the carrier particle that is bound to the sample substance to the capture part 40 after the capture part 40 captures the carrier particle and the sample substance, and the sample substance that is bound can be separated from the sample substance that is not bound.

Second Embodiment of Fluidic Device

A fluidic device of a second embodiment has a circulation mixer of a second embodiment.

First, the second embodiment of the circulation mixer is described.

Figure 2:
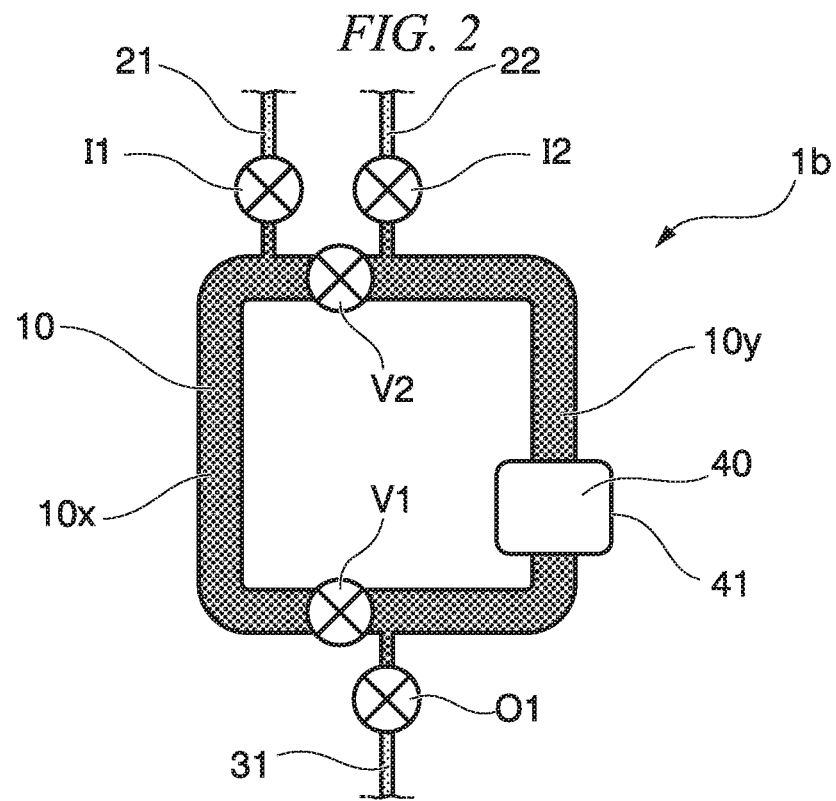
FIG. 2 is a plan view showing a schematic configuration of a fluidic device according to an embodiment of the present invention.

FIG. 2 is a plan view showing a circulation mixer of the second embodiment. In the second embodiment, the same reference numerals are given to the same elements as the configuration elements of the first embodiment, and description of the elements is omitted.

A circulation mixer 1b of the second embodiment includes a circulation flow path 10, and an introduction flow path 21 (first introduction flow path) through which first liquid is introduced and an introduction flow path 22 (second introduction flow path) through which second liquid is introduced are connected to the circulation flow path 10. An introduction flow path valve I1 that opens and closes the introduction flow path 21 is provided on the introduction flow path 21. An introduction flow path valve I2 that opens and closes the introduction flow path 22 is provided on the introduction flow path 22. The second circulation flow path valve V2 is arranged between the introduction flow path 21 and the introduction flow path 22 and in the vicinity of the introduction flow path 21 and the introduction flow path 22.

The first introduction flow path 21, the second introduction flow path 22, and the discharge flow path 31 are configured such that a different solution can be introduced to each of partitions of the circulation flow path 10.

According to the circulation mixer 1b of the second embodiment, operations and effects similar to the first embodiment described above can be obtained, and additionally, by operating opening and closing of the introduction flow path valves I1, I2, it is possible to control filling of liquid, air, or the like with respect to the flow paths 10x, 10y inside the circulation flow path 10 partitioned by the circulation flow path valves V1, V2 individually in a state where the first liquid and the second liquid are partitioned. Thereby, it is possible to accurately control a mixing reaction of the first liquid and the second liquid. For example, when the first liquid includes an antibody, and the second liquid includes an antigen, it is possible to prevent an antigen-antibody reaction from occurring until the circulation flow path valves V1, V2 are opened.

For example, in the circulation mixer 1b, a third circulation flow path valve V3 (not shown) may be further provided on the circulation flow path 10, and the discharge flow path 31 may be connected to the circulation flow path 10 between the first circulation flow path valve V1 and the third circulation flow path valve V3. It is possible to control discharging and filling of liquid, air, and the like from the circulation flow path 10 partitioned by the circulation flow path valve individually by operating opening and closing of the third circulation flow path valve V3. In this case, the introduction of the solution can be described, for example, as below. First, in a state where the second circulation flow path valve V2 and the third circulation flow path valve V3 are closed, and the introduction flow path valve I1, the first circulation flow path valve V1, and the discharge flow path valve O1 are open, the first liquid is introduced from the first introduction flow path 21. The first liquid is discharged to the discharge flow path 31 through the flow path 10x. Then, the first circulation flow path valve V1 is closed, and the first liquid is filled to the flow path 10x without passing through the flow path 10y. Next, the third circulation flow path valve is opened, and the second liquid is introduced from the second introduction flow path 22. Then, the second liquid is discharged to the discharge flow path 31 through the flow path 10y. Then, the discharge valve O1 is closed, and the second liquid is filled to the flow path 10y without passing through the flow path 10x. In this way, by providing the third circulation flow path valve V3, it is possible to prevent the first liquid and the second liquid from unnecessarily coming into contact with each other before being mixed.

Third Embodiment of Fluidic Device

A fluidic device of a third embodiment has a circulation mixer of a third embodiment.

First, the third embodiment of the circulation mixer is described.

Figure 3:
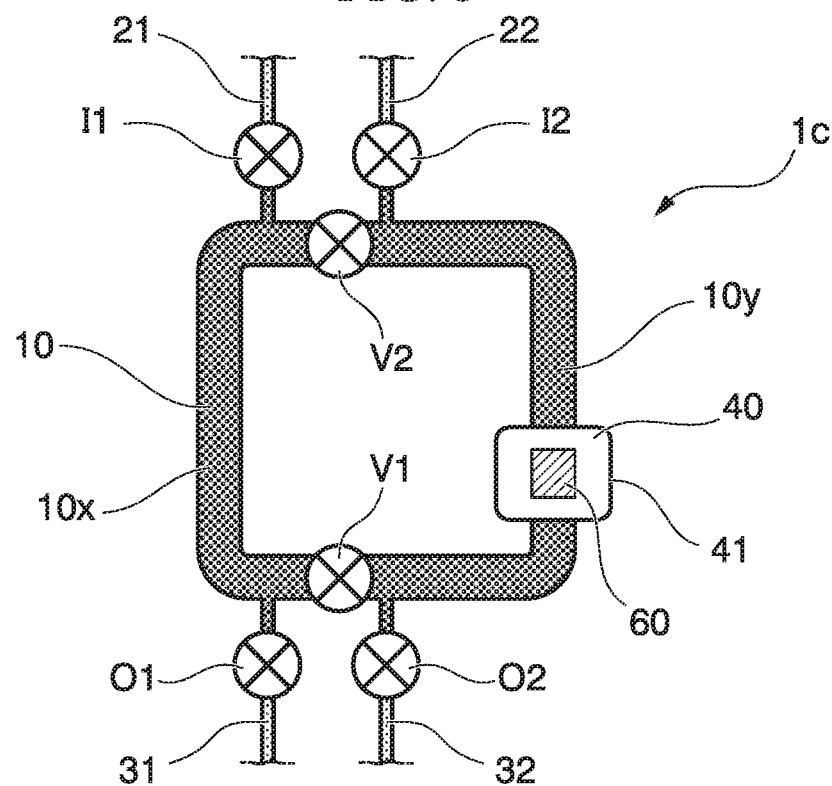
FIG. 3 is a plan view showing a schematic configuration of a fluidic device according to an embodiment of the present invention.

FIG. 3 is a plan view showing a circulation mixer of the third embodiment. In the third embodiment, the same reference numerals are given to the same elements as the configuration elements of the second embodiment, and description of the elements is omitted.

A circulation mixer 1c of the third embodiment includes a circulation flow path 10, and a discharge flow path 31 and a discharge flow path 32 are connected to the circulation flow path 10. A discharge flow path valve O1 that opens and closes the discharge flow path 31 is provided on the discharge flow path 31. A discharge flow path valve O2 that opens and closes the discharge flow path 32 is provided on the discharge flow path 32. The circulation flow path valve V1 is arranged between the discharge flow path 31 and the discharge flow path 32 and in the vicinity of the discharge flow path 31 and the discharge flow path 32. The circulation mixer 1c of the third embodiment further includes a detection part 60.

The detection part 60 is arranged on the circulation flow path 10 and detects a sample substance in a solution that is circulated in the circulation flow path 10. The detection part 60 may detect a sample substance that is bound to a carrier particle. Hereinafter, a case is described in which a sample substance is bound to a carrier particle.

The detection part 60 is arranged to be directed to a capture part 40 such that the sample substance that is bound to the carrier particle which is captured by the capture part 40 can be detected. Here, the capture part 40 and the detection part 60 are arranged at the same position of the circulation flow path 10.

The detection part 60 may have any configuration as long as the detection part 60 can detect the sample substance, and, for example, the detection part 60 may optically detect the sample substance. As an example, the detection part 60 may include an objective lens or an imaging part. The imaging part may include, for example, an EMCCD (Electron-Multiplying Charge-Coupled Device) camera.

Alternatively, the detection part 60 may electrochemically detect the sample substance and may include, as an example, an electrode.

Detecting a sample substance includes detecting a sample substance indirectly. As an example of detecting a sample substance indirectly, a sample substance may be bound to a detection aid substance that aids detection of the sample substance. Examples of the detection aid substance include a labeling substance.

Examples of the labeling substance include fluorescent pigments, fluorescent beads, fluorescent proteins, quantum dots, gold nanoparticles, biotin, antibodies, antigens, energy absorption materials, radioisotopes, chemiluminescent bodies, and enzymes.

Examples of the fluorescent pigments include carboxyfluorescein (FAM), 6-carboxy-4',5'-dichloro-2',7'-dimethoxy fluorescein (JOE), fluorescein isothiocyanate (FITC), tetrachloro fluorescein (TET), 5'-hexachloro-fluorescein-CE phosphoroamidite (HEX), Cy3, Cy5, Alexa 568, and Alexa 647.

Examples of the enzymes include alkaline phosphatase and peroxidase.

The sample substance can be detected by detecting the labeling substance using the detection part 60. When using an enzyme as the labeling substance, the sample substance can be detected by detecting a reaction product such as a pigment or fluorescence generated by the reaction with a substrate using the detection part 60.

For example, by circulating a solution that includes a sample substance and a solution that includes a detection aid substance in the circulation flow path 10 and binding the sample substance and the detection aid substance, it is possible to perform pretreatment for sample substance detection.

In the present embodiment, the detection part 60 is arranged to be directed to the capture part 40, and the capture part 40 and the detection part 60 are arranged at the same position of the circulation flow path 10; however, the detection part may not be arranged to be directed to the capture part 40 depending on the detection method. The position of the detection part 60 in the circulation flow path is arbitrary.

In the present embodiment, the circulation mixer c includes two introduction flow paths and two discharge flow paths; however, even in a case of a circulation mixer that includes the detection part 60 and the capture part 40, the number of the introduction flow path and the discharge flow path is arbitrary. For example, as shown in the circulation mixers 1a, 1b, the number of the introduction flow path may be one or two, and the number of the discharge flow path may be one.

According to the circulation mixer 1c of the third embodiment, operations and effects similar to the second embodiment described above can be obtained, and additionally, by operating opening and closing of the discharge flow path valves O1, O2, it is possible to control discharge and filling of liquid, air, or the like with respect to the flow paths 10x, 10y inside the circulation flow path 10 partitioned by the circulation flow path valves V1, V2 individually. Further, since the detection part 60 is provided on the circulation flow path 10, the detection chance of the sample substance that is bound to the carrier particle is prompted, and it is possible to detect the sample substance with high efficiency.

(Mix Method Using Circulation Mixer 1a)

A mix method of a first embodiment is described with reference to FIGS. 4A to 4E. The mix method of the first embodiment is a mix method using the circulation mixer 1a of the first embodiment. First, in a state where the circulation flow path valves V1, V2 and the discharge flow path valve O1 of the circulation mixer 1a are open (refer to FIG. 4A), first liquid 91 is sent from the introduction flow path 21 to the inside of the circulation flow path 10 (refer to FIG. 4B). Next, the circulation flow path valves V1, V2 are closed, and the flow path 10x and the flow path 10y are partitioned (refer to FIG. 4C). Thereby, the first liquid 91 having the volume of the partition of the flow path 10x is filled in the flow path 10x. Then, second liquid 92 is sent from the introduction flow path 21 to the inside of the circulation flow path 10y (refer to FIG. 4D). Thereby, the second liquid 92 is filled in the flow path 10y. The discharge valve O1 is closed, and the second liquid 92 having the volume of the flow path 10y is filled to the flow path 10y (refer to FIG. 4D). The circulation flow path valves V1, V2 are opened, and the first liquid 91 and the second liquid 92 are circulated inside the circulation flow path 10 and are mixed to obtain third liquid 93 (refer to FIG. 4E).

According to the mix method of the first embodiment, partitioning and communicating of the circulation flow path 10 are controlled by the opening and closing of the circulation flow path valves V1, V2, and thereby, it is possible to determine the quantity of the first liquid 91 and the second liquid 92 and to mix the first liquid 91 and the second liquid 92.

(Mix Method Using Circulation Mixer 1c)

A mix method of a second embodiment is described with reference to FIGS. 4F to H. The mix method of the second embodiment is a mix method using the circulation mixer 1c of the third embodiment. The mix method of the present embodiment includes an introduction step and a mix step.

The introduction step is a step in which, in a state where the two circulation flow path valves are closed, a solution that includes a sample substance is introduced to one of partitions partitioned by the circulation flow path valve, and a solution that includes a carrier particle which is bound to the sample substance is introduced to the other of the partitions.

Figure 4A:
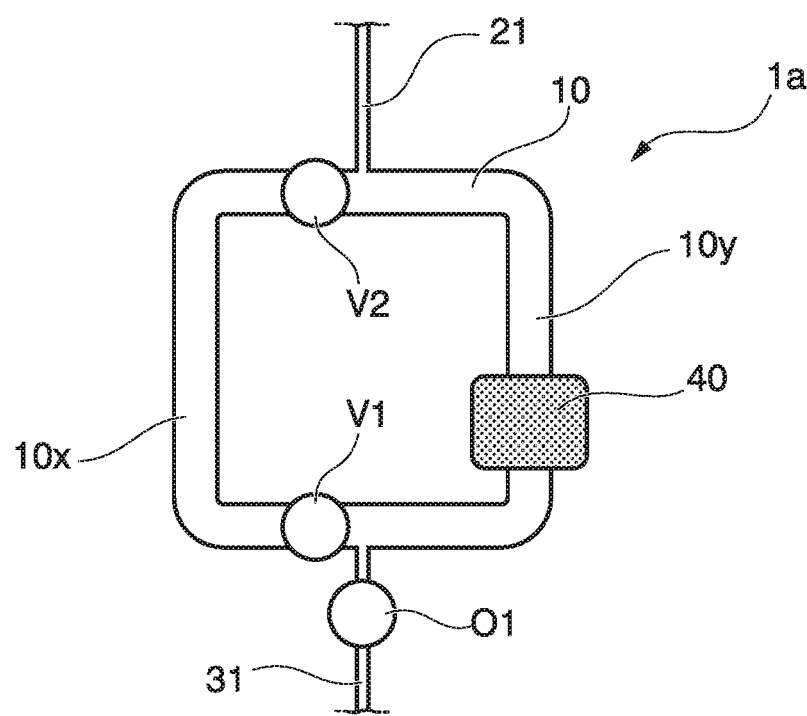
FIG. 4A is a view showing a sequence of a mix method using a fluidic device according to an embodiment of the present invention.
Figure 4B:
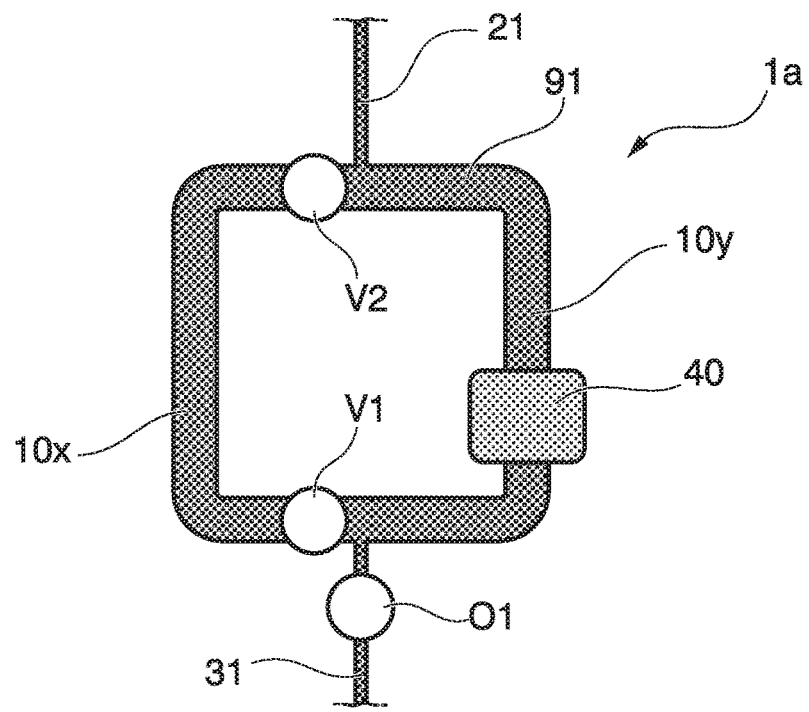
FIG. 4B is a view showing the sequence of the mix method using the fluidic device according to the embodiment of the present invention.
Figure 4C:
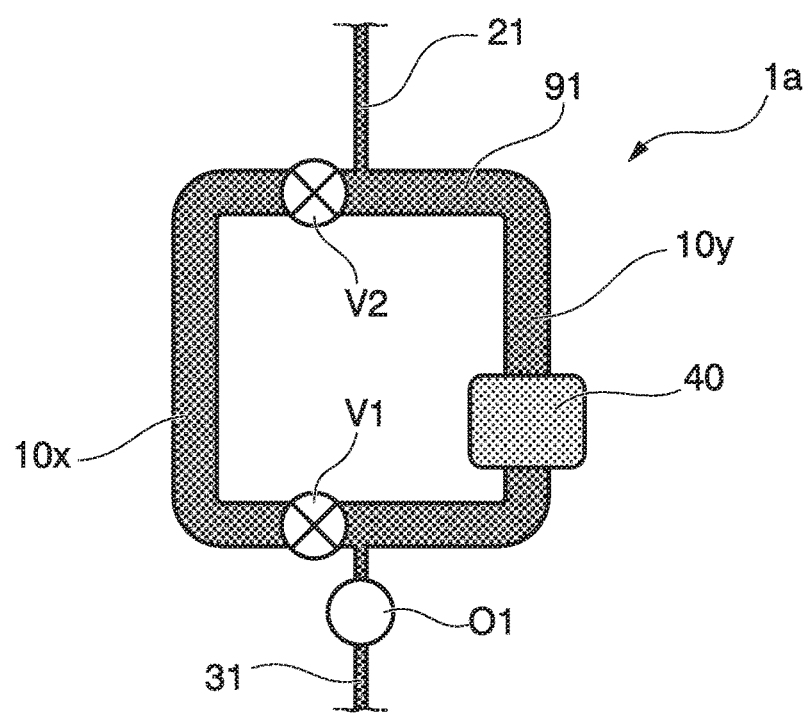
FIG. 4C is a view showing the sequence of the mix method using the fluidic device according to the embodiment of the present invention.
Figure 4D:
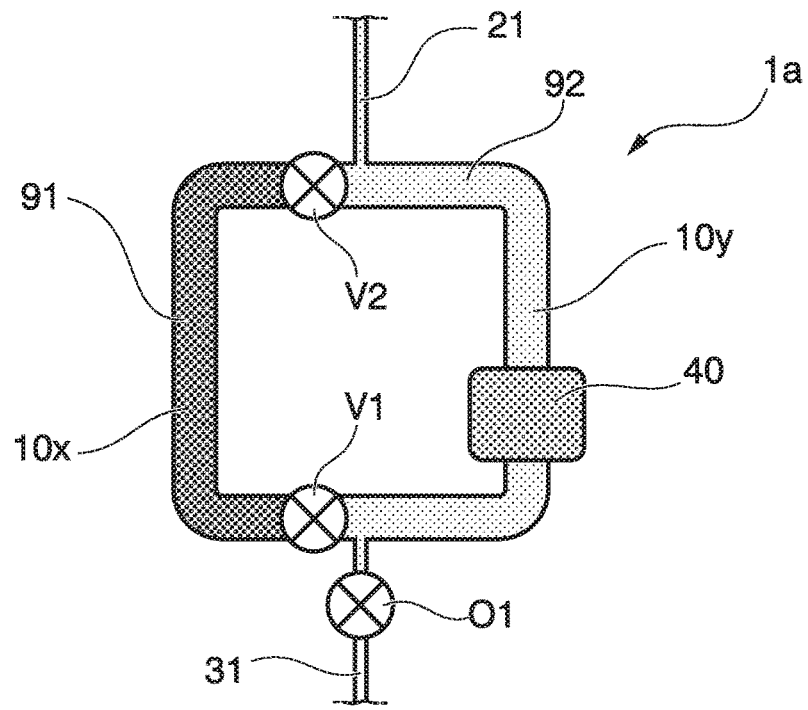
FIG. 4D is a view showing the sequence of the mix method using the fluidic device according to the embodiment of the present invention.
Figure 4E:
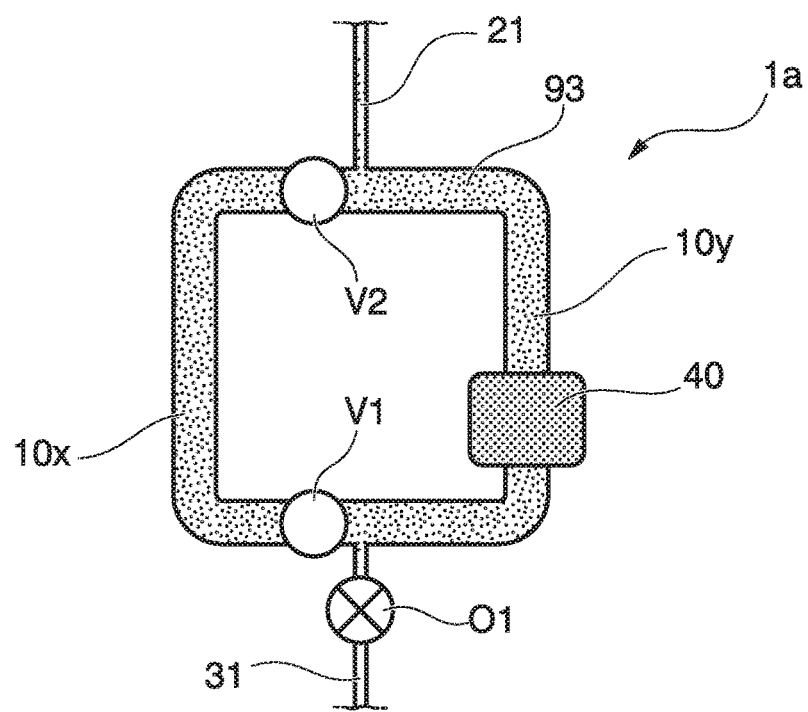
FIG. 4E is a view showing the sequence of the mix method using the fluidic device according to the embodiment of the present invention.
Figure 4F:
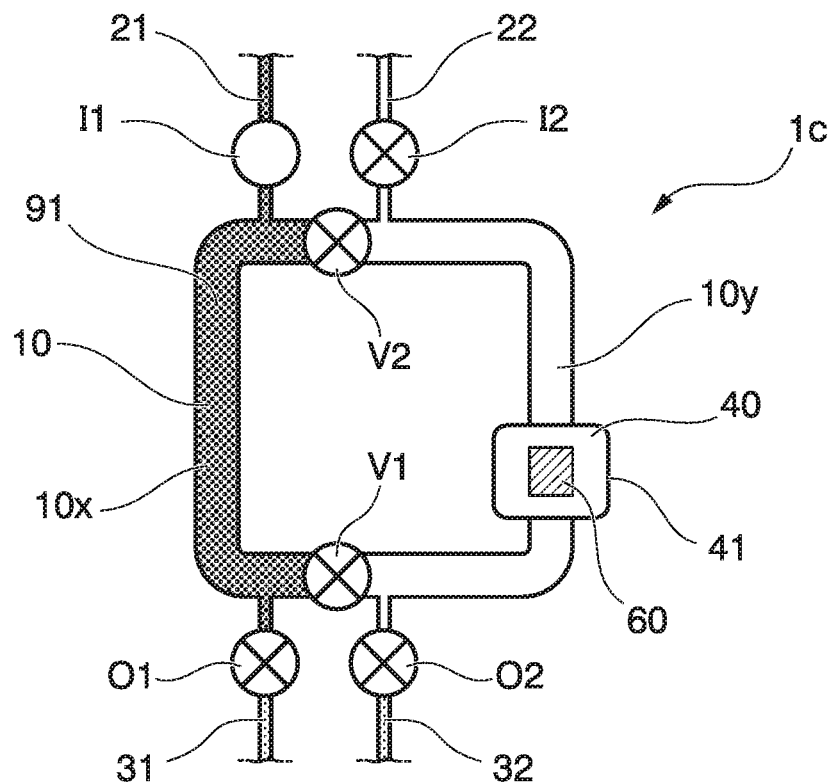
FIG. 4F is a view showing a sequence of a method using a fluidic device according to an embodiment of the present invention.
Figure 4G:
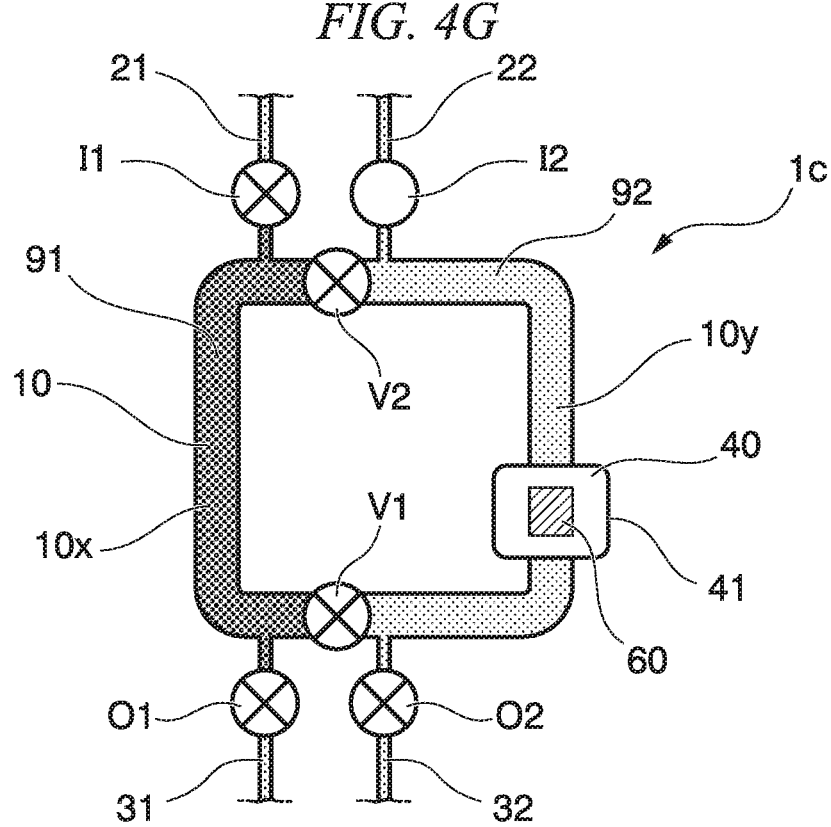
FIG. 4G is a view showing the sequence of the method using the fluidic device according to the embodiment of the present invention.
Figure 4H:
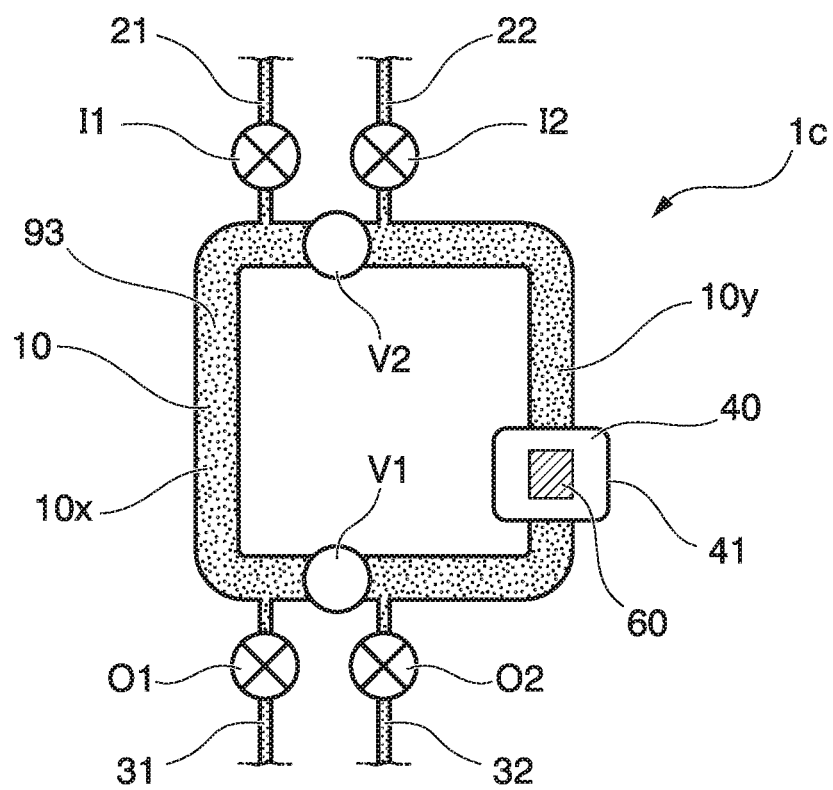
FIG. 4H is a view showing the sequence of the method using the fluidic device according to the embodiment of the present invention.

First, in a state where the introduction flow path valves I1, I2 and the discharge flow path valves O1, O2 of the circulation mixer 1c are open, and the circulation flow path valves V1, V2 are closed, first liquid 91 that includes a sample substance is sent from the introduction flow path 21 to the inside of the circulation flow path 10x (refer to FIG. 4F). By closing the discharge flow path valve O1 and, if necessary, the introduction flow path valve I1, the first liquid 91 having the volume of the partition of the flow path 10x is filled in the flow path 10x. On the other hand, second liquid 92 that includes a carrier particle is sent from the introduction flow path 22 to the inside of the circulation flow path 10y. By closing the discharge flow path valve O2 and, if necessary, the introduction flow path valve I2, the second solution 92 having the volume of the partition of the flow path 10y is filled to the flow path 10y (refer to FIG. 4G).

The mix step is a step in which all of the circulation flow path valves are opened, and the solution is circulated and is mixed in the circulation flow path. That is, the circulation flow path valves V1, V2 are opened, and the first liquid 91 and the second liquid 92 are circulated inside the circulation flow path 10 and are mixed to obtain third liquid 93 (refer to FIG. 4H).

(Capture Method Using Circulation Mixer 1c)

A capture method of an embodiment is a method using the circulation mixer 1c of the third embodiment and is a method in which a sample substance that is bound to a carrier particle is captured. The present method includes an introduction step, a mix step, and a capture step. Examples of the introduction step and the mix step include those described in the "(Mix Method using Circulation Mixer 1c)".

The capture step is a step in which the carrier particle is captured by the capture part.

The third liquid 93 obtained in the mix step includes a complex of the sample substance and the carrier particle, and the carrier particle is captured by the capture part 40 to thereby capture the sample substance by the capture part 40.

(Detection Method Using Circulation Mixer 1c)

A detection method of an embodiment is a method using the circulation mixer 1c of the third embodiment and is a method in which a sample substance that is bound to a carrier particle is detected. The present method includes an introduction step, a mix step, a capture step, and a detection step. Examples of the introduction step, the mix step, and the capture step include those described in the "(Mix Method using Circulation Mixer 1c)" and the "(Capture Method using Circulation Mixer 1c)".

The detection step is a step in which the sample substance that is bound to the carrier particle captured by the capture part is detected by the detection part.

The detection part 60 detects the presence of the sample substance that is bound to the carrier particle captured by the capture part 40 in the capture step.

Fourth Embodiment of Fluidic Device

A fluidic device of an embodiment has a circulation mixer of a fourth embodiment.

First, the fourth embodiment of the circulation mixer is described. The circulation mixer of the present embodiment includes the circulation flow path (first circulation flow path) 10 and further at least one circulation flow path (second circulation flow path) 50 that is different from the circulation flow path 10.

A capture part that captures a sample substance in a solution is arranged on the first circulation flow path.

A detection part that detects the sample substance in the solution is arranged on the second circulation flow path.

The circulation mixer may include a connection flow path that directly or indirectly connects the first circulation flow path and the second circulation flow path.

Figure 5:
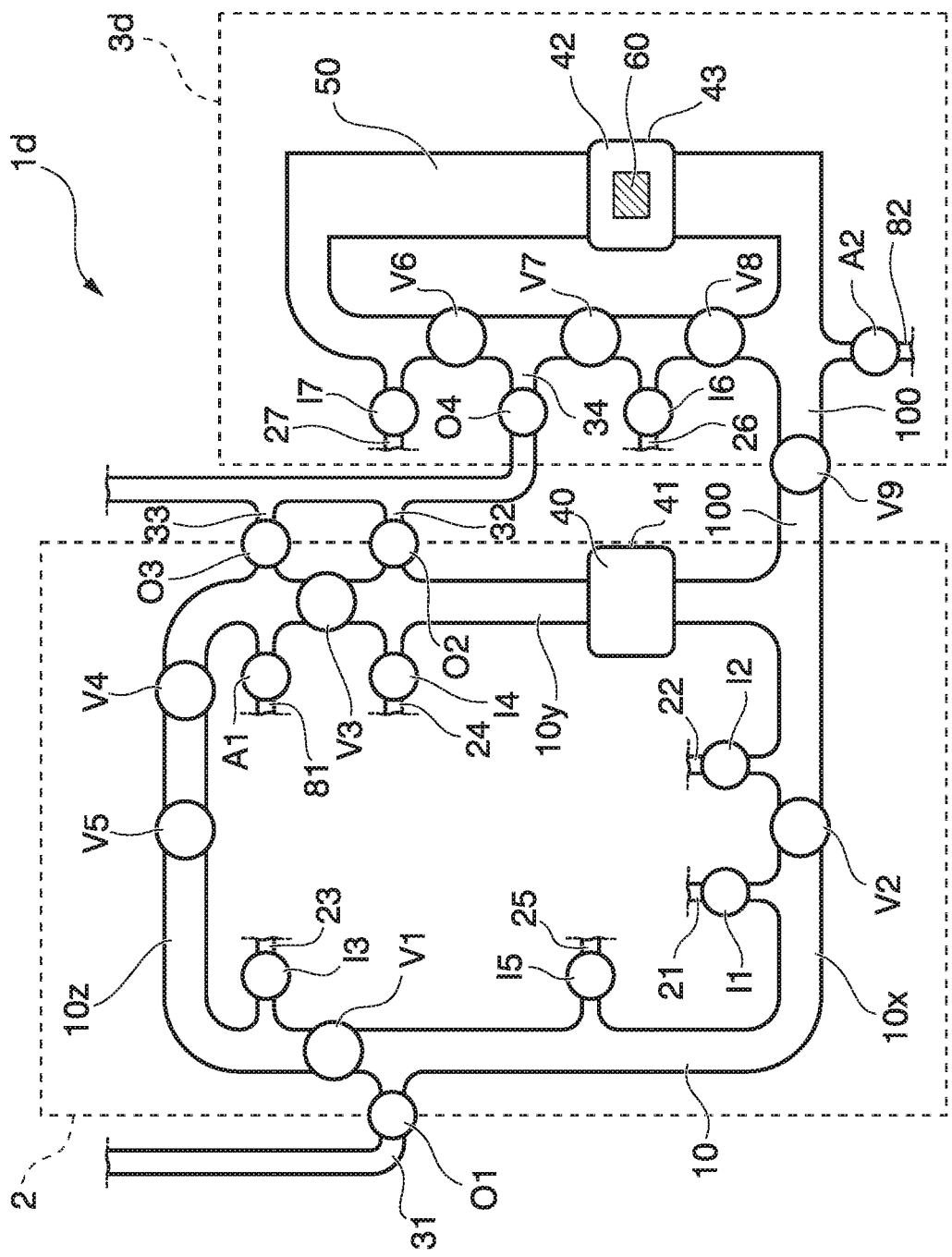
FIG. 5 is a plan view showing a schematic configuration of a fluidic device according to an embodiment of the present invention.

FIG. 5 is a plan view showing the circulation mixer of the fourth embodiment. In the fourth embodiment, the same reference numerals are given to the same elements as the configuration elements of the third embodiment, and description of the elements is omitted.

A circulation mixer 1d of the fourth embodiment includes a first circulation flow path 10 in which liquid that includes a carrier particle is circulated and a second circulation flow path 50 in which liquid that is introduced from the first circulation flow path 10 is circulated. Circulation flow path valves V1, V2, V3 are arranged on the first circulation flow path 10. The second circulation flow path 50 includes a detection part 60 which detects a sample substance that is bound to a carrier particle.

In the first circulation flow path 10, by causing the sample substance to circulate and causing the sample substance to be bound to a detection aid substance, it is possible to perform pretreatment for sample substance detection. The sample substance applied with the pretreatment is sent from the first circulation flow path 10 to the second circulation flow path 50. The sample substance applied with the pretreatment is detected in the second circulation flow path 50. The sample substance applied with the pretreatment is circulated in the second circulation flow path 50 to thereby come into contact with the detection part 60 repeatedly and is efficiently detected.

The detection part 60 is arranged to be directed to a capture part 42 such that the sample substance that is bound to the carrier particle which is captured by the capture part 42 can be detected. Examples of the capture part 42 include those described for the above capture part 40. In the present embodiment, the detection part 60 is arranged to be directed to the capture part 42, and the capture part 42 and the detection part 60 are arranged at the same position of the second circulation flow path 50; however, the detection part may not be arranged to be directed to the capture part 42 depending on the detection method. The position of the detection part 60 in the second circulation flow path 50 is arbitrary.

Introduction flow paths 21, 22, 23, 24, 25 each introducing first to fifth liquid are connected to the first circulation flow path 10. One of introduction flow path valves I1, I2, I3, I4, I5 that open and close the introduction flow path is provided on each of the introduction flow paths 21, 22, 23, 24, 25.

An introduction flow path 81 that introduces air is connected to the first circulation flow path 10, and an introduction flow path valve A1 that opens and closes the introduction flow path is provided on the introduction flow path 81.

Discharge flow paths 31, 32, 33 are connected to the first circulation flow path 10. One of discharge flow path valves O1, O2, O3 that open and close the discharge flow path is provided on each of the discharge flow paths 31, 32, 33.

A first circulation flow path valve V1, a second circulation flow path valve V2, and a third circulation flow path valve V3 that partition the circulation flow path 10 are provided on the circulation flow path 10. The first circulation flow path valve V1 is arranged in the vicinity of the discharge flow path 31. The second circulation flow path valve V2 is arranged between the introduction flow path 21 and the introduction flow path 22 and in the vicinity of the introduction flow path 21 and the introduction flow path 22. The third circulation flow path valve V3 is arranged between the discharge flow path 32 and the discharge flow path 33 and in the vicinity of the discharge flow path 32 and the discharge flow path 33.

In this way, the circulation flow path 10 is partitioned into three flow paths 10x, 10y, 10z when the first circulation flow path valve V1, the second circulation flow path valve V2, and the third circulation flow path valve V3 are closed, and at least one introduction flow path and at least one discharge flow path are connected to each partition.

Introduction flow paths 26, 27 are connected to the second circulation flow path 50. One of introduction flow path valves I6, I7 that open and close the introduction flow path is provided on each of the introduction flow paths 26, 27.

An introduction flow path 82 that introduces air is connected to the second circulation flow path 50, and an introduction flow path valve A2 that opens and closes the introduction flow path is provided on the introduction flow path 82.

A discharge flow path 34 is connected to the second circulation flow path 50. A discharge flow path valve O4 that opens and closes the discharge flow path is provided on the discharge flow path 34.

Pump valves V4, V5 are provided on the circulation flow path 10. The third circulation flow path valve V3 is also used as a pump valve. Pump valves V6, V7, V8 are provided on the second circulation flow path 50.

The second circulation flow path 50 may be partitioned into two or more partitions each having a predetermined volume by two or more circulation flow path valves. Although the valves V6, V7, V8 are pump valves in the circulation mixer 1d of the fourth embodiment, the second circulation flow path 50 may be partitioned when these valves are closed. The aspect described in the circulation flow path 10 of the embodiment can be employed for partitioning the second circulation flow path using the valve.

The volume inside the second circulation flow path 50 may be smaller than the volume inside the first circulation flow path 10. The volume inside the circulation flow path is a volume inside the circulation flow path when liquid is circulated in the circulation flow path. As an example, the volume inside the first circulation flow path 10 is a volume inside the circulation flow path 10 when the valves V1, V2, V3, V4, V5 are opened, and the valves I1, I2, I3, I4, I5, O1, O2, O3, A1, V9 are closed. As an example, the volume inside the second circulation flow path 50 is a volume inside the second circulation flow path 50 when the valves V6, V7, V8 are opened, and the valves I6, I7, O4, A2, V9 are closed.

The volume inside the second circulation flow path 50 is smaller than the volume inside the circulation flow path 10, and thereby, the amount of liquid that is circulated in the second circulation flow path 50 is smaller than the amount of liquid that is circulated in the circulation flow path 10. Therefore, it is possible to reduce the usage amount of an agent used for detection. Further, the volume inside the second circulation flow path 50 is smaller than the volume inside the circulation flow path 10, and thereby, it is possible to improve the detection sensitivity. For example, when a detection target object is dispersed or dissolved in the liquid inside the second circulation flow path 50, the liquid amount inside the second circulation flow path 50 is made small to thereby condense the detection target object, and therefore, it is possible to improve the detection sensitivity.

Further, the volume inside the second circulation flow path 50 may be larger than the volume inside the circulation flow path 10. In this case, the amount of liquid that is circulated in the second circulation flow path 50 is larger than the amount of liquid that is circulated in the circulation flow path 10. In this case, for example, the liquid that is circulated in the circulation flow path 10 is transported to the second circulation flow path 50, and it is possible to further add measurement liquid or a substrate solution.

The first circulation flow path 10 and the second circulation flow path 50 are connected by a connection flow path 100. A connection flow path valve V9 that opens and closes the connection flow path 100 is provided on the connection flow path 100. The pretreatment or the like is performed by circulating liquid in the circulation flow path 10 in a state where the connection flow path valve V9 is closed. Then, the connection flow path valve V9 is opened, and the liquid is sent to the second circulation flow path via the connection flow path. Then, the connection flow path valve V9 is closed, and the liquid is circulated in the second circulation flow path to perform detection reaction. Thereby, after required pretreatment is performed, a sample after the pretreatment is sent to the second circulation flow path, and therefore, it is possible to prevent an unnecessary substance from being circulated in the second circulation flow path 50. Therefore, it is possible to prevent contamination and noise at the time of detection. Further, the first circulation flow path 10 and the second circulation flow path 50 do not share a flow path in which liquid can be circulated. According to the first circulation flow path 10 and the second circulation flow path 50 not sharing the flow path in which circulation can be performed, a possibility that a residual substance which is adhered to a wall surface inside the circulation flow path 10 is circulated in the second circulation flow path 50 is reduced, and it is possible to reduce contamination at the time of detection by the second circulation flow path 50 caused by a residual substance remaining inside the circulation flow path 10.

The fluidic device may include one circulation flow path or equal to or more than two circulation flow paths that are different from the first circulation flow path 10 and the second circulation flow path 50.

According to the circulation mixer 1d of the fourth embodiment, operations and effects similar to the third embodiment described above can be obtained, and additionally, the detection part 60 is provided on the second circulation flow path 50 that is a circulation flow path which is different from the circulation flow path 10 in which a plurality of types of liquid are circulated and mixed. Therefore, mixing of liquid as the pretreatment of detection and detection of a sample substance are performed in a different circulation flow path, and thereby, a condition used for mixing as the pretreatment for detecting the sample substance and a condition used for detection can be independently selected for each circulation flow path.

Accordingly, the efficiency of mixing of liquid and detection of the sample substance is improved.

In the second circulation flow path 50, a substrate solution, measurement liquid, and the like may be further added to and mixed with the liquid which is mixed in the circulation flow path 10 and is then introduced to the second circulation flow path 50.

Fifth Embodiment of Fluidic Device

Figure 6:
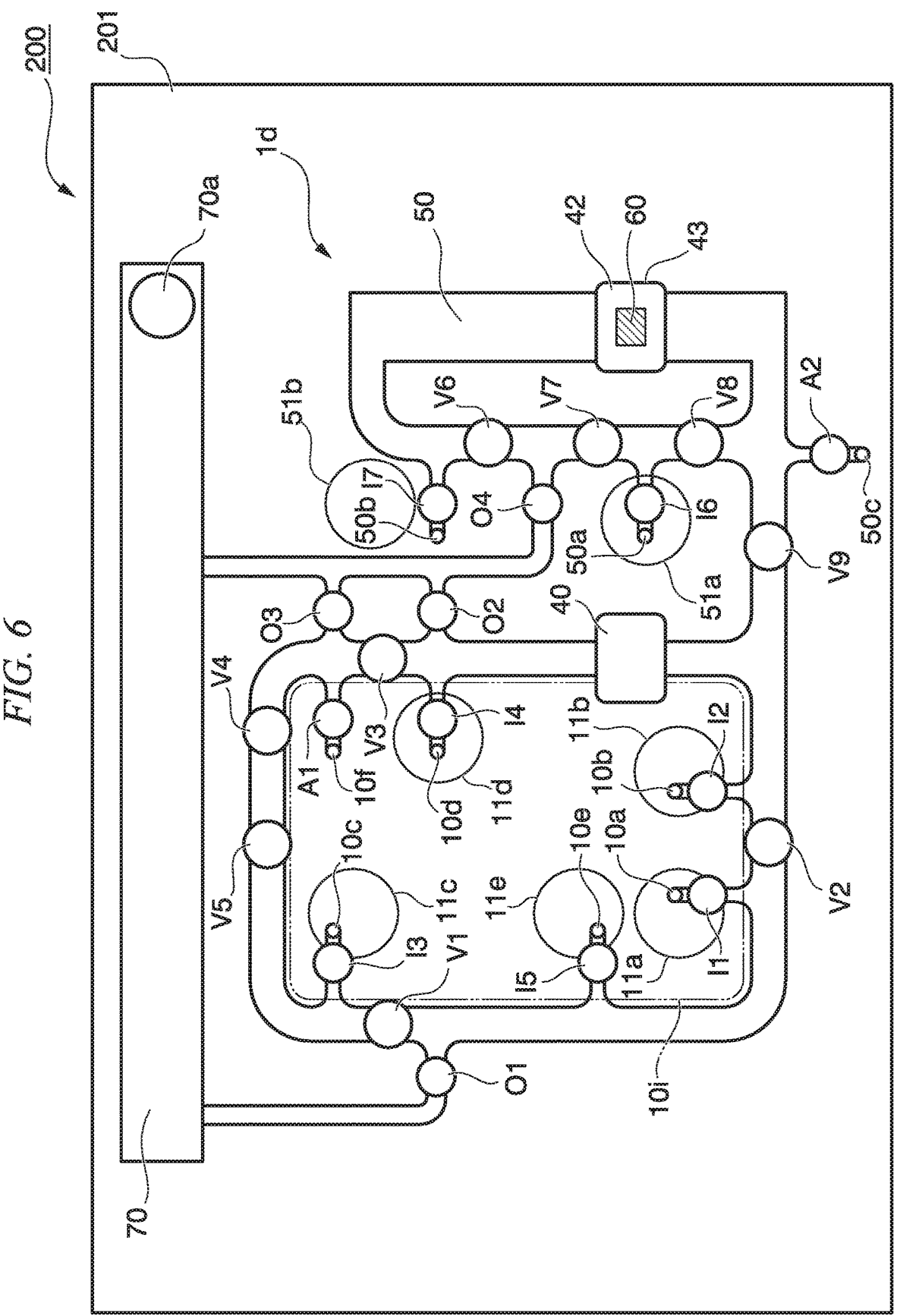
FIG. 6 is a plan view showing a schematic configuration of a fluidic device according to an embodiment of the present invention.

FIG. 6 is a plan view showing a fluidic device of a fifth embodiment.

A fluidic device 200 of the fifth embodiment includes a circulation mixer 1d. The same reference numerals are given to the same elements as the configuration elements of the fourth embodiment of the circulation mixer, and description of the elements is omitted.

The fluidic device 200 is a device that detects an antigen (sample substance, biomolecule) as a detection target included in an analyte sample by immune reaction and enzyme reaction.

The fluidic device 200 is a substrate in which a flow path and a valve that constitute the circulation mixer 1d are formed. For example, the fluidic device 200 may be formed by bonding a substrate 201 in which a flow path is formed to a substrate in which a reservoir is formed. Although the substrate in which the reservoir is formed is not shown in FIG. 6, the position of the reservoir is shown for ease of understanding.

The fluidic device 200 includes an introduction inlet separately for a sample, a reagent, and air to be introduced.

The fluidic device 200 includes a first reagent introduction inlet 10a, an analyte introduction inlet 10b, a second reagent introduction inlet 10c, a cleaning liquid introduction inlet 10d, a transport liquid introduction inlet 10e, and an air introduction inlet 10f.

The first reagent introduction inlet 10a opens at the surface of the substrate 201 and is connected to a reservoir 11a formed on the substrate that is bonded to the substrate 201. A first reagent accommodated in the reservoir 11a is introduced to the first circulation flow path 10 via the first reagent introduction inlet 10a.

The analyte introduction inlet 10b opens at the surface of the substrate 201 and is connected to a reservoir 11b formed on the substrate that is bonded to the substrate 201. An analyte accommodated in the reservoir 11b is introduced to the first circulation flow path 10 via the analyte introduction inlet 10b.

The second reagent introduction inlet 10c opens at the surface of the substrate 201 and is connected to a reservoir 11c formed on the substrate that is bonded to the substrate 201. A second reagent accommodated in the reservoir 11c is introduced to the first circulation flow path 10 via the second reagent introduction inlet 10c.

As shown in FIG. 6, a connection part to the circulation flow path 10 of the introduction flow path through which the first reagent is introduced and a connection part to the circulation flow path 10 of the introduction flow path through which the analyte is introduced are arranged close to each other. More specifically, the connection part to the circulation flow path 10 of the introduction flow path through which the first reagent is introduced is arranged closer to the connection part to the circulation flow path 10 of the introduction flow path through which the analyte is introduced than a connection part to the circulation flow path 10 of an introduction flow path through which the second reagent is introduced. According to this configuration, reaction between the first reagent and the analyte is prompted.

The cleaning liquid introduction inlet 10d opens at the surface of the substrate 201 and is connected to a reservoir 11d formed on the substrate that is bonded to the substrate 201. Cleaning liquid accommodated in the reservoir 11d is capable of being introduced to the first circulation flow path 10 via the cleaning liquid introduction inlet 10d.

The transport liquid introduction inlet 10e opens at the surface of the substrate 201 and is connected to a reservoir 11e formed on the substrate that is bonded to the substrate 201. Transport liquid accommodated in the reservoir 11e is introduced to the circulation flow path 10 via the transport liquid introduction inlet 10e.

The air introduction inlet 10f opens at the surface of the fluidic device, and air can be introduced to the circulation flow path 10 via the opening.

The fluidic device 200 includes a substrate solution introduction inlet 50a, a measurement liquid introduction inlet 50b, and an air introduction inlet 50c.

The substrate solution introduction inlet 50a opens at the surface of the substrate 201 and is connected to a reservoir 51a formed on the substrate that is bonded to the substrate 201. A substrate solution accommodated in the reservoir 51a is introduced to the second circulation flow path 50 via the substrate solution introduction inlet 50a.

The measurement liquid introduction inlet 50b opens at the surface of the substrate 201 and is connected to a reservoir 51b formed on the substrate that is bonded to the substrate 201. Measurement liquid accommodated in the reservoir 51b is introduced to the second circulation flow path 50 via the measurement liquid introduction inlet 50b.

The air introduction inlet 50c opens at the surface of the fluidic device, and air can be introduced to the second circulation flow path 50 from the introduction flow path 82 via the opening.

Discharge flow paths 31, 32, 33 are connected to a waste liquid tank 70. The waste liquid tank 70 includes an outlet 70a. The outlet 70a opens at the surface of the fluidic device 200 and is connected, as an example, to an external suction pump (not shown), and negative pressure suction can be performed.

The inlets 10a, 10b, 10c, 10d, 10e, 10f and the reservoirs 11a, 11b, 11c, 11d, 11e may be arranged at a circulation flow path inner region 10i, which is an inner part of the first circulation flow path 10, and may be arranged at an outer part of the first circulation flow path. The circulation flow path 10 preferably has a certain amount of flow path length from the viewpoint of mixing and quantitative determination. Therefore, a configuration for introducing an analyte and reagents can be arranged in the circulation flow path inner region 10i. The configurations for the analyte and reagents introduced to the circulation flow path 10 are collectively arranged, and thereby, the configuration of the introduction port through which the liquid that is introduced to the circulation flow path 10 is introduced can be made compact. On the other hand, depending on the size of the reservoir or the like, the reservoir and the inlet may be arranged outside the first circulation flow path.

The waste liquid tank 70 is arranged outside the circulation flow path 10. By arranging the waste liquid tank 70 in a circulation flow path outer region, a discharge part such as a reservoir space of waste liquid and the outlet is easily ensured. Further, when only liquid is discharged from the waste liquid tank 70, by arranging the waste liquid tank 70 in the circulation flow path outer region, the waste liquid process becomes easy. As an alternative method, the waste liquid tank may be formed on a substrate that is different from the substrate 201, and in that case, it is also possible to arrange the waste liquid tank regardless of the position of the first circulation flow path.

In the circulation mixer 1d, the second circulation flow path 50 is arranged outside the first circulation flow path; however, the second circulation flow path 50 may be arranged in the circulation flow path inner region 10i.

Figure 7:
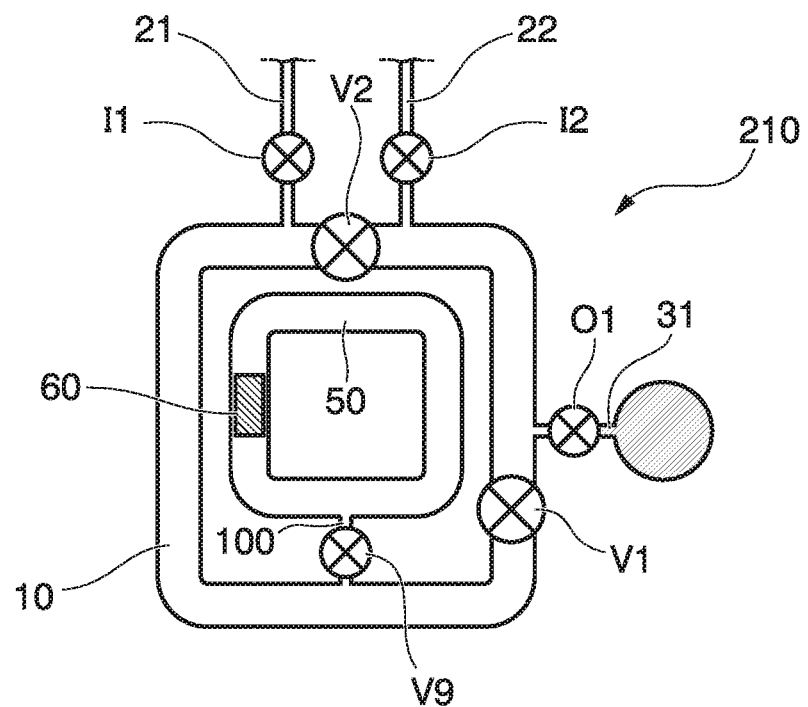
FIG. 7 is a plan view showing a schematic configuration of a fluidic device according to an embodiment of the present invention.

Conversely, the first circulation flow path 10 may be arranged in the inner region of the second circulation flow path 50. For example, a fluidic device 210 shown in FIG. 7 has a double structure in which the first circulation flow path 10 and the second circulation flow path 50 are connected to each other via a connection flow path, and, for example, liquid mixed in the circulation flow path 10, which is an outer loop structure, may be introduced to the second circulation flow path 50, which is an inner loop structure. At this time, the inlet and the reservoir may be arranged outside the circulation flow path 10, which is the outer loop structure, and may be arranged inside the circulation flow path 10 and outside the second circulation flow path 50. According to such a configuration, the space of the circulation mixer can be reduced, and a compact fluidic device can be realized.

(Mix Method, Capture Method, and Detection Method Using Fluidic Device 200)

Next, a mix method, a capture method, and a detection method using the fluidic device 200 having the above-described configuration are described. The fluidic device 200 includes the circulation mixer 1d, and therefore, a mix method, a capture method, and a detection method using the circulation mixer 1d are described below. Each of the circulation flow path valves in the circulation mixer 1d is arranged such that each of the partitions of the circulation flow path partitioned by the circulation flow path valves has a predetermined volume.

In the capture method of the present embodiment, a sample substance that is bound to a carrier particle is captured. In the detection method of the present embodiment, a sample substance that is bound to a carrier particle is detected by immune reaction and enzyme reaction of an antigen (sample substance, biomolecule) as a detection target included in an analyte sample.

(Introduction Step, Partitioning Step)

A method of the present embodiment includes an introduction step in which, in a state where the circulation flow path valve of the first circulation flow path is closed, a solution that includes a sample substance is introduced to at least one of partitions partitioned by the first circulation flow path valve, and a solution that includes a carrier particle which is bound to the sample substance is introduced to at least another of the partitions.

The first circulation flow path has three circulation flow path valves. In the introduction step, the solution that includes the sample substance is introduced to one partition, the solution that includes the carrier particle which is bound to the sample substance is introduced to one partition, and a solution that includes a detection aid substance is introduced to one partition.

Figure 8:
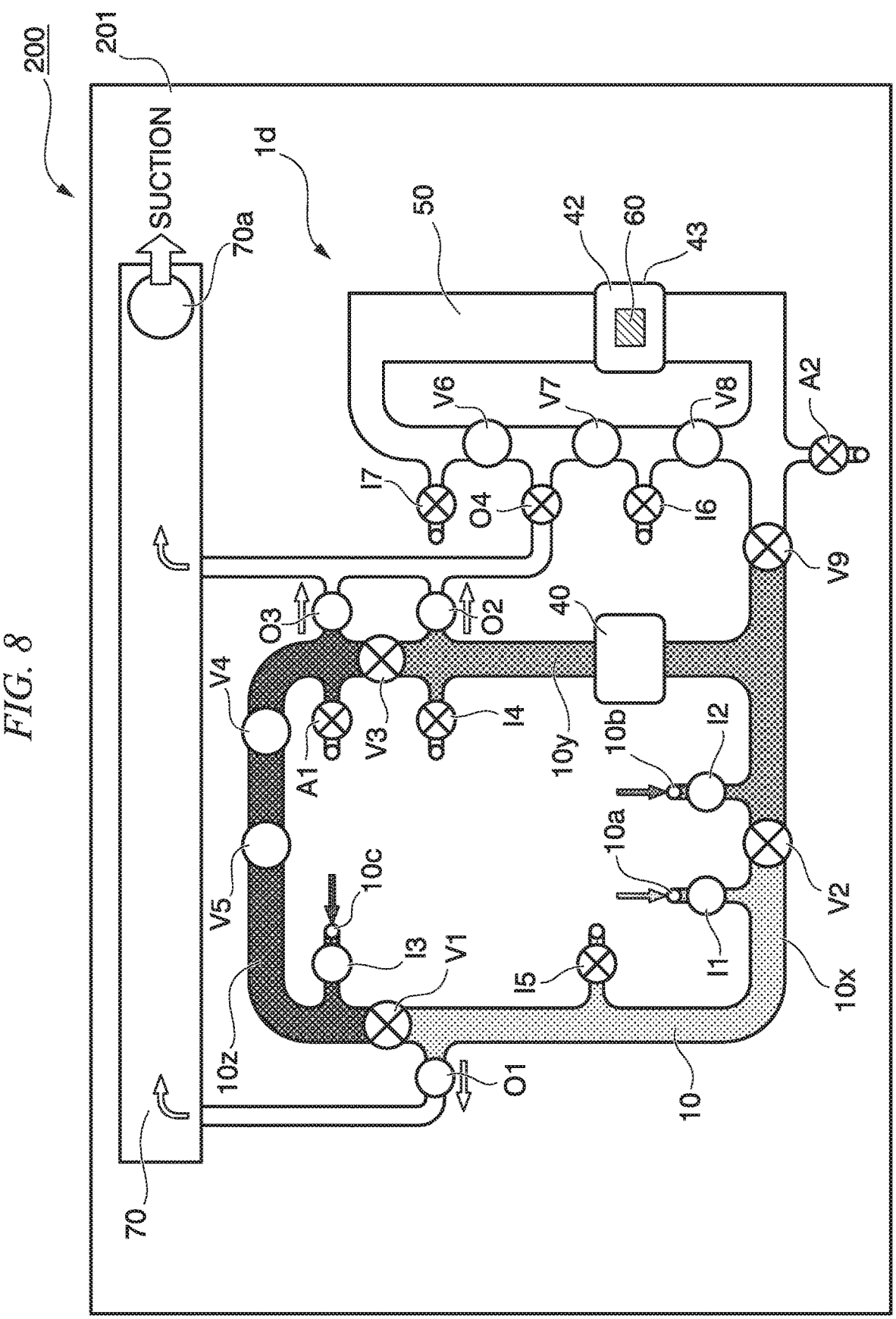
FIG. 8 is a view showing a sequence of a mix method, a capture method, and a detection method using the fluidic device according to the embodiment of the present invention.

First, as shown in FIG. 8, in a state where the introduction flow path valves I1, I2, I3 are opened, and the first circulation flow path valve V1, the second circulation flow path valve V2, and the third circulation flow path valve V3 are closed, a first reagent is introduced from the first reagent introduction inlet 10a, an analyte is introduced from the analyte introduction inlet 10b, and a second reagent is introduced from the second reagent introduction inlet 10c. At this time, the introduction flow path valves I5, I4, A1 are closed.

In this way, the first reagent is introduced to the flow path 10x of the circulation flow path 10 partitioned by the first circulation flow path valve V and the second circulation flow path valve V2. The analyte is introduced to the flow path 10y of the circulation flow path 10 partitioned by the second circulation flow path valve V2 and the third circulation flow path valve V3. The second reagent is introduced to the flow path 10z of the circulation flow path 10 partitioned by the third circulation flow path valve V3 and the first circulation flow path valve V1.

The first reagent contains a magnetic particle (carrier particle). An antibody A to be specifically bound to an antigen (sample substance) as the detection target is immobilized to the surface of the magnetic particle. The analyte contains the antigen as the detection target. Examples of the analyte include a body fluid such as blood, urine, saliva, blood plasma, and blood serum, cell extract, and tissue breakage fluid. The second reagent contains an antibody B to be specifically bound to an antigen as the detection target. Alkaline phosphatase (detection aid substance, enzyme) is immobilized to the antibody B, and the antibody B is labeled.

(Mix Step)

Next, all of the circulation flow path valves of the first circulation flow path are opened, and the solution is circulated and is mixed in the first circulation flow path. This step is described.

Figure 9:
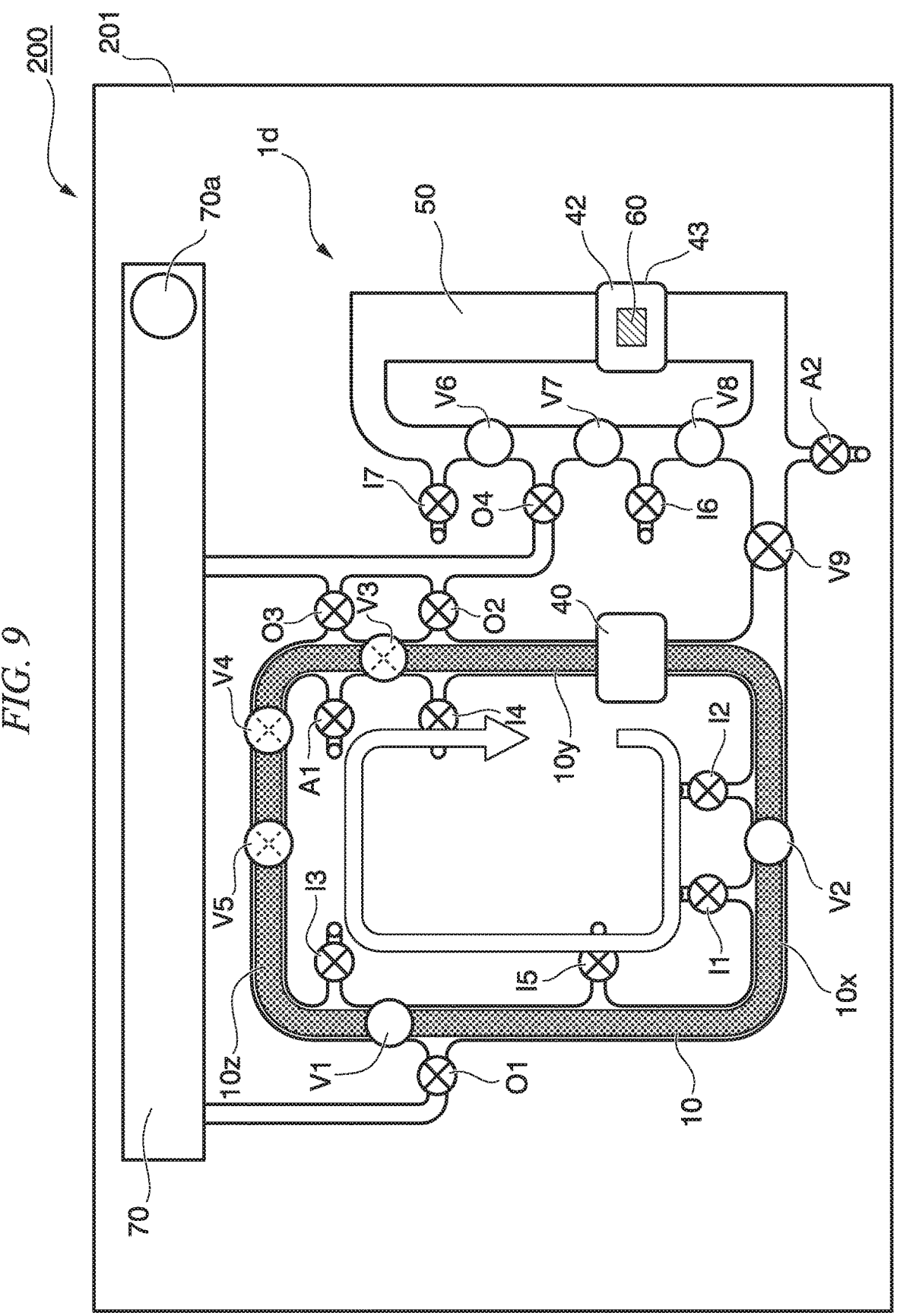
FIG. 9 is a view showing a sequence of the mix method, the capture method, and the detection method using the fluidic device according to the embodiment of the present invention.

First, as shown in FIG. 9, the introduction flow path valves I1, I2, I3 are closed. The connection flow path valve V9 is closed. Thereby, the communication of the first circulation flow path 10 with the flow path connected to the first circulation flow path 10 is cut off, and the first circulation flow path 10 is isolated. Then, the first circulation flow path valve V1, the second circulation flow path valve V2, and the third circulation flow path valve V3 are opened, the pump valves V3, V4, V5 are operated, the first reagent, the analyte, and the second reagent are circulated and mixed in the circulation flow path 10, and the mixed liquid of the first reagent, the analyte, and the second reagent is obtained. By the mixing of the first reagent, the analyte, and the second reagent, an antigen is bound to the antibody A that is immobilized to the carrier particle, and the antibody B to which the enzyme is immobilized is bound to the antigen. Thereby, in the mix step, a carrier particle-antigen-enzyme complex is formed. In this way, in the mix step, a carrier particle-sample substance-detection aid substance complex is obtained.

(Magnet Arrangement Step, Capture Step)

Next, a capture step in which the carrier particle is captured by the capture part is described.

The capture part 40 includes a magnet arrangement part 41 at which a magnet that captures a magnetic particle can be arranged. The magnet arrangement part 41 is configured such that the magnetic force of the magnet can be controlled. When the magnetic force of the magnet of the magnet arrangement part is enhanced, and the solution is circulated, the carrier particle is captured by the capture part. For example, the magnet is arranged at the magnet arrangement part 41, and the magnet is in a state in which the magnet is close to the circulation flow path and capture can be performed. In this state, the pump valves V3, V4, V5 are operated, the liquid that includes the carrier particle-antigen-enzyme complex is circulated in the circulation flow path 10, and the carrier particle-antigen-enzyme complex is captured by the capture part 40. The carrier particle-antigen-enzyme complex flows in one direction or both directions in the circulation flow path and is circulated or reciprocated in the circulation flow path. FIG. 9 shows a state in which the carrier particle-antigen-enzyme complex circulates in one direction. The complex is captured on an inner wall surface of the circulation flow path 10 at the capture part and is isolated from the liquid constituent.

(Cleaning Step)

Next, a step in which the carrier particle captured by the capture part is cleaned is described.

The introduction flow path valve A1 and the discharge flow path valve O2 are opened, the third circulation flow path valve V3 is closed, negative pressure suction is performed through the outlet 70a, and air is introduced from the air introduction inlet 10f into the circulation flow path 10. Thereby, the liquid constituent (waste liquid) separated from the carrier particle-antigen-enzyme complex is discharged from the first circulation flow path 10 via the discharge flow path 32. The waste liquid is reserved in the waste liquid tank 70. By closing the third circulation flow path valve V3, air is efficiently introduced to the entire circulation flow path 10.

Then, the discharge flow path valve O2 and the third circulation flow path valve V3 are closed, the introduction flow path valve I4 and the discharge flow path valve O3 are opened, negative pressure suction is performed through the outlet 70a, and cleaning liquid is introduced from the cleaning liquid introduction inlet 10d into the first circulation flow path 10. By closing the third circulation flow path valve V3, the cleaning liquid is introduced so as to fill the first circulation flow path 10.

The third circulation flow path valve V3 is opened, the introduction flow path valve I4 and the discharge flow path valve O2 are closed to close the circulation flow path 10, the pump valves V3, V4, V5 are operated, the cleaning liquid is circulated in the circulation flow path 10, and the carrier particle is cleaned.

Subsequently, the introduction flow path valve A1 and the discharge flow path valve O2 are opened, the third circulation flow path valve V3 is closed, negative pressure suction is performed through the outlet 70a, and air is introduced from the air introduction inlet 10f into the circulation flow path 10. Thereby, the cleaning liquid is discharged from the circulation flow path 10, and an antibody B that does not form the carrier particle-antigen-enzyme complex is discharged from the circulation flow path 10.

The introduction of the cleaning liquid and discharge may be performed a plurality of times. By repeatedly introducing the cleaning liquid, performing cleaning, and discharging the liquid after cleaning, the removal efficiency of an unnecessary substance is enhanced.

(Transport Step)

Next, a transport step in which the carrier particle is released from the capture part, and a solution that includes a sample substance that is released or is bound to the carrier particle is transported to the second circulation flow path via the connection flow path is described.

The introduction flow path valve I5 and the discharge flow path valve O3 are opened, the discharge flow path valve O2 and the third circulation flow path valve V3 are closed, negative pressure suction is performed through the outlet 70a, and transport liquid is introduced from the transport liquid introduction inlet 10e into the circulation flow path 10.

Further, the introduction flow path valve I5 and the discharge flow path valve O2 are opened, the discharge flow path valve O3 and the third circulation flow path valve V3 are closed, negative pressure suction is performed through the outlet 70a, and transport liquid is introduced from the transport liquid introduction inlet 10e into the circulation flow path 10.

Subsequently, the third circulation flow path valve V3 is opened, the introduction flow path valve I5 and the discharge flow path valves O2, O3 are closed to close the circulation flow path 10. Then, the magnet is detached from the magnet arrangement part 41 and is caused to be away from the circulation flow path, and the capture of the carrier particle-antigen-enzyme complex captured on the inner wall surface of the circulation flow path 10 is released. The pump valves V3, V4, V5 are operated, the transport liquid is circulated in the circulation flow path 10, and the carrier particle-antigen-enzyme complex is dispersed in the transport liquid. In this way, in the transport step, the solution that includes the carrier particle-sample substance-detection aid substance complex is transported to the second circulation flow path.

In the present embodiment, the sample substance together with the carrier particle is released from the capture part 40; however, the sample substance may be released from the carrier particle while capturing the carrier particle, the sample substance may be caused to be included in the transport liquid, and the sample substance may be detected by the detection part in the subsequent detection step.

Figure 10:
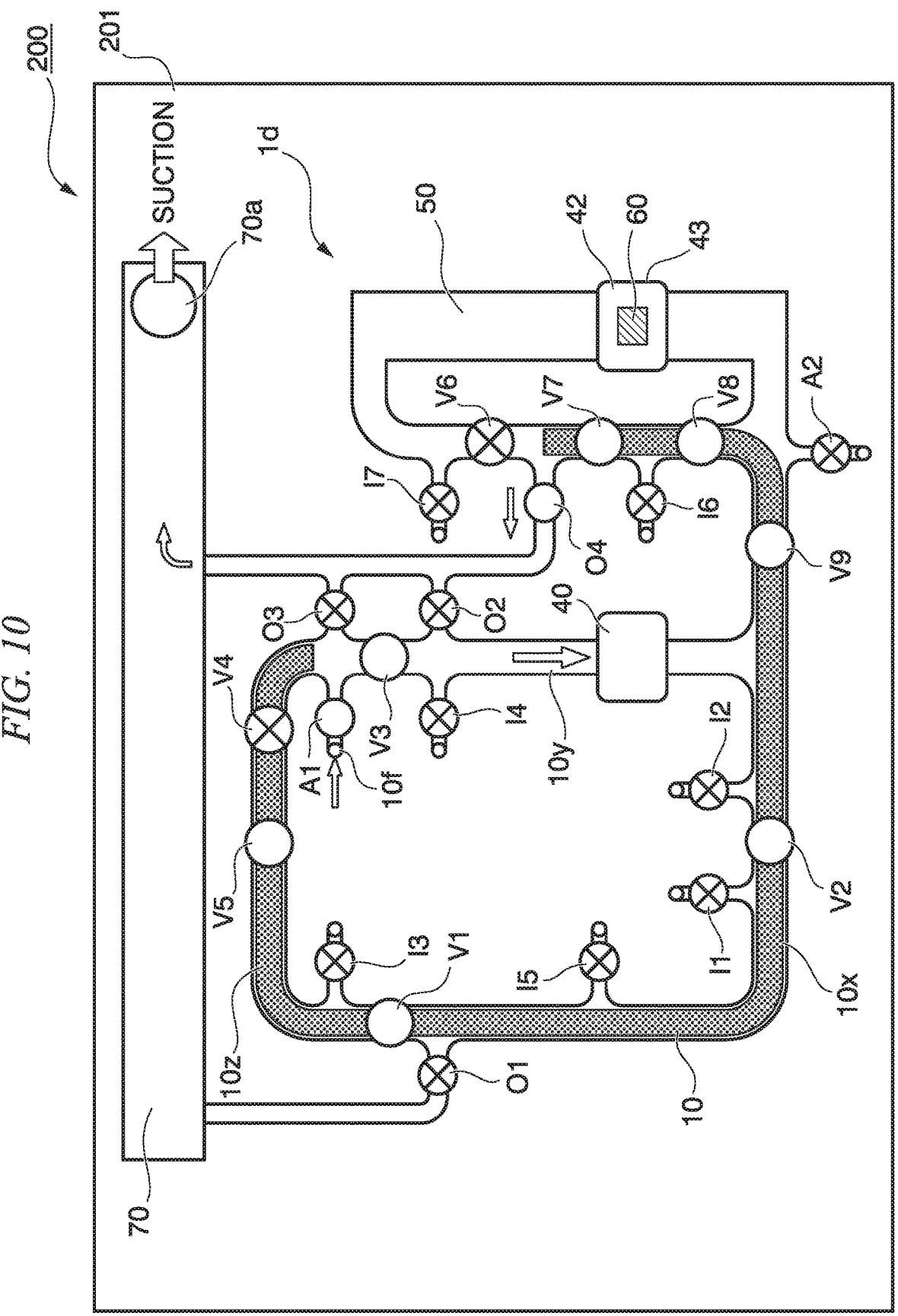
FIG. 10 is a view showing a sequence of the mix method, the capture method, and the detection method using the fluidic device according to the embodiment of the present invention.

Subsequently, as shown in FIG. 10, the introduction flow path valve A1, the connection flow path valve V9, and the discharge flow path valve O4 are opened, negative pressure suction is performed through the outlet 70a, and air is introduced into the circulation flow path 10 via the air introduction inlet 10f. The transport liquid that includes the carrier particle-antigen-enzyme complex is pushed out by air and is introduced to the second circulation flow path 50 via the connection flow path 100. At this time, the valve V6 is closed. When the transport liquid arrives at the connection part between the discharge flow path 34 and the second circulation flow path 50, the valve V7 is closed in turn, and the inside of the second circulation flow path 50 is filled with the transport liquid. The carrier particle-antigen-enzyme complex is transported to the second circulation flow path 50. At least part of the transport liquid may be introduced to at least one of the partitions.

At least two circulation flow path valves (pump valve) of the second circulation flow path 50 may be closed to compartmentalize the second circulation flow path 50 into two or more partitions, and at least part of the transport liquid may be introduced to at least one of the partitions. In that case, a reagent required for detection is filled in another partition in advance, the circulation flow path valve is opened to mix the transport liquid and the reagent, and then, it is possible to perform detection.

In the present embodiment, in the transport step, the connection flow path valve V9 is opened; however, the connection flow path valve may be opened prior to the transport step.

(Detection Step)

Figure 11:
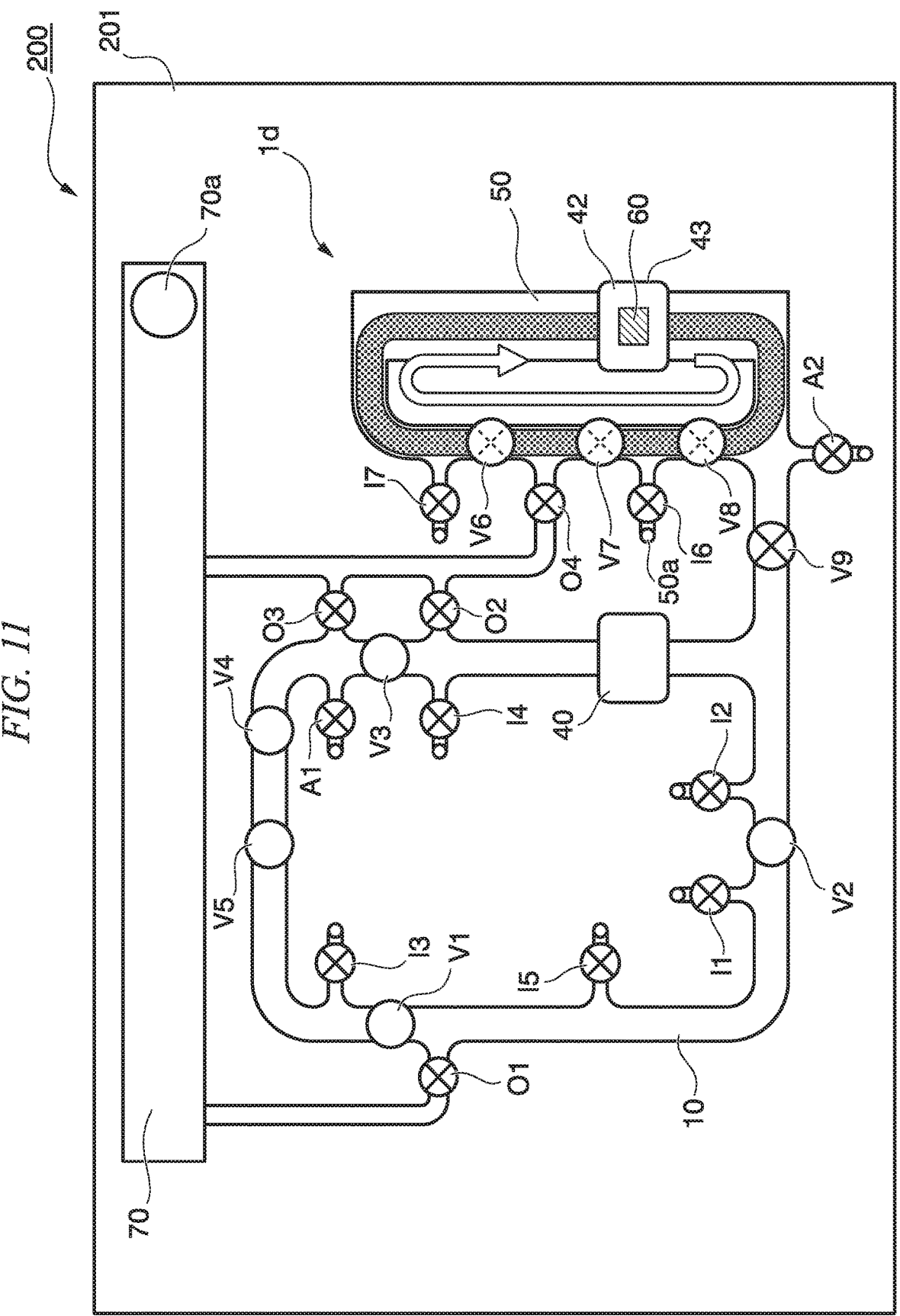
FIG. 11 is a view showing a sequence of the mix method, the capture method, and the detection method using the fluidic device according to the embodiment of the present invention.

Next, a detection step in which the sample substance that is bound to the carrier particle captured by the capture part is detected by the detection part is described. After the transport of the transport liquid to the second circulation flow path 50 is completed, as shown in FIG. 11, the connection flow path valve V9 and the discharge flow path valve O4 are closed to close the second circulation flow path 50, the pump valves V6, V7, V8 are operated, the transport liquid is circulated in the second circulation flow path 50, and the carrier particle-antigen-enzyme complex is captured by the capture part 42.

The introduction flow path valve A2 and the discharge flow path valve O4 are opened, negative pressure suction is performed through the outlet 70a, and air is introduced into the second circulation flow path 50 via the introduction flow path 82 from the air introduction inlet 50c. Thereby, the liquid constituent (waste liquid) of the transport liquid separated from the carrier particle-antigen-enzyme complex is discharged from the second circulation flow path 50 via the discharge flow path 34. The waste liquid is reserved in the waste liquid tank 70. At this time, by closing the valve V6 or V7, air is efficiently introduced to the entire second circulation flow path 50.

Prior to the detection, a solution that includes the detection aid substance may be introduced to at least another of the partitions. The introduction flow path valve I6 and the discharge flow path valve O4 are opened, the valve V7 is closed, negative pressure suction is performed through the outlet 70a, and the substrate solution is introduced into the second circulation flow path 50 via the introduction flow path 26 from the substrate solution introduction inlet 50a. The substrate solution includes 3-(2'-spiroadamantane)-4-methoxy-4-(3"-phosphoryloxy) phenyl-1,2-dioxetane (AM-PPD), 4-aminophenyl phosphate (pAPP), or the like which becomes a substrate of alkaline phosphatase (enzyme).

The discharge flow path valve O4 and the introduction flow path valve I6 are closed to close the second circulation flow path 50, the pump valves V6, V7, V8 are operated, and the substrate solution is circulated in the second circulation flow path 50 and is caused to react with the enzyme of the carrier particle-antigen-enzyme complex. The detection may be performed while performing circulation.

According to the operation described above, it is possible to detect, at the detection part 60, the antigen of the detection target included in the analyte as a chemiluminescence emission signal, an electrochemical signal, or the like. In this way, in the detection step, the carrier particle-sample substance-detection aid substance complex is detected.

In the present embodiment, a case in which the detection part 60 is arranged on the second circulation flow path is described. As described in this case, the detection part and the capture part may not be used in combination, and it is not essential to provide the capture part on the second circulation flow path 50. The detection part and the capture part may be arranged at the same position on the second circulation flow path 50, the detection part and the capture part may be combined, and the detection part 60 may detect the substance captured by the capture part 42.

Alternatively, a metal ion that is precipitated as a metal by insolubilization reaction with pAPP as a substrate of alkaline phosphatase (enzyme) is introduced into the second circulation flow path 50. The discharge flow path valve O4 and the introduction flow path valve I6 are closed to close the second circulation flow path 50, the pump valves V6, V7, V8 are operated, the substrate solution is circulated in the second circulation flow path 50 and is caused to react with the enzyme of the carrier particle-antigen-enzyme complex, and the metal is deposited on the detection part. Similarly to the above description, air is introduced from the air introduction inlet 50c, and the substrate solution (waste liquid) is discharged from the second circulation flow path 50 via the discharge flow path 34.

The introduction flow path valve I7 and the discharge flow path valve O4 are opened, the valve V6 is closed, negative pressure suction is performed through the outlet 70a, and measurement liquid is introduced into the second circulation flow path 50 via the introduction flow path 27 from the measurement liquid introduction inlet 50b. The measurement liquid includes a strong electrolysis solution and the like as a substance having a role of enhancing the signal.

The discharge flow path valve O4 and the introduction flow path valve I7 are closed to close the second circulation flow path 50, the pump valves V6, V7, V8 are operated, the measurement liquid is circulated in the second circulation flow path 50, and the deposited metal amount is electrically analyzed.

The detection method of the present embodiment is also applicable to the analysis of a biological sample, in vitro diagnostic, or the like.

The procedure of opening and closing of the valve in the mix method, the capture method, and the detection method of the present embodiment is shown in Table 1.

TABLE 1

| | | V1 | V2 | V3 | V4 | V5 | I1 | I2 | I3 | I4 | I5 | A1 | O1 | O2 | O3 | V9 | V6 | V7 | V8 | I6 | I7 | A2 | O4 |
|---|---|---|---|---|---|---|---|---|---|---|---|---|---|---|---|---|---|---|---|---|---|---|---|
| 1 | PARTITIONING/INTRODUCTION STEP | C | C | C | O | O | O | O | O | C | C | C | O | O | O | C | O | O | O | C | C | C | C |
| 2 | CLOSE STEP | C | C | C | O | O | C | C | C | C | C | C | C | C | C | C | O | O | O | C | C | C | C |
| 3 | MIX STEP | O | O | Open-Close | C | C | C | C | C | C | C | C | C | C | C | C | O | O | O | C | C | C | C |
| 4 | CAPTURE STEP | O | O | Open-Close | C | C | C | C | C | C | C | C | C | C | C | C | O | O | O | C | C | C | C |
| 5 | CLEANING STEP (MIXED LIQUID DISCHARGE) | O | O | C | O | O | C | C | C | C | C | O | C | O | C | C | O | O | O | C | C | C | C |
| 6 | (CLEANING LIQUID INTRODUCTION 1) | O | O | C | O | O | C | C | C | O | C | C | C | O | C | C | O | O | O | C | C | C | C |
| 7 | (CLEANING LIQUID INTRODUCTION 2) | O | O | C | O | O | C | C | C | C | C | C | C | C | C | O | O | O | O | C | C | C | C |
| 8 | CLEANING STEP (CARRIER PARTICLE CLEANING) | O | O | Open-Close | C | C | C | C | C | C | C | C | C | C | C | C | O | O | O | C | C | C | C |
| 9 | (CLEANING LIQUID DISCHARGE) | O | O | C | O | O | C | C | C | C | C | O | C | O | C | O | O | O | O | C | C | C | C |
| 10 | TRANSPORT STEP (TRANSPORT LIQUID INTRODUCTION 1) | O | O | C | O | O | C | C | C | C | O | C | C | C | O | C | O | O | O | C | C | C | C |
| 11 | (TRANSPORT LIQUID INTRODUCTION 2) | O | O | C | O | O | C | C | C | C | O | C | C | O | C | C | O | O | O | C | C | C | C |
| 12 | (CARRIER PARTICLE DISPERSION) | O | O | Open-Close | C | C | C | C | C | C | C | C | C | C | C | O | O | O | C | C | C | C |
| 13 | (TRANSPORT 1) | O | O | O | C | O | C | C | C | C | C | O | C | C | C | O | C | O | O | C | C | C | O |
| 14 | (TRANSPORT 2) | O | O | C | O | O | C | C | C | C | O | C | C | C | O | O | C | O | C | C | C | C | O |
| 15 | DETECTION STEP (DETECTION PART PARTICLE CAPTURE) | O | O | O | O | O | C | C | C | C | C | C | C | C | C | C | Open-Close | C | C | C | C |
| 16 | (TRANSPORT LIQUID DISCHARGE 1) | O | O | O | O | O | C | C | C | C | C | C | C | C | C | C | O | O | C | C | O | O |

TABLE 1-continued

| | V1 | V2 | V3 | V4 | V5 | I1 | I2 | I3 | I4 | I5 | A1 | O1 | O2 | O3 | V9 | V6 | V7 | V8 | I6 | I7 | A2 | O4 |
|---|---|---|---|---|---|---|---|---|---|---|---|---|---|---|---|---|---|---|---|---|---|---|
| 17 (TRANSPORT LIQUID DISCHARGE 2) | O | O | O | O | O | C | C | C | C | C | C | C | C | C | C | O | C | O | C | C | O | O |
| 18 (SUBSTRATE SOLUTION INTRODUCTION) | O | O | O | O | O | C | C | C | C | C | C | C | C | C | C | O | C | O | O | C | C | O |
| 19 (SUBSTRATE SOLUTION CIRCULATION) | O | O | O | O | O | C | C | C | C | C | C | C | C | C | C | Open-Close | C | C | C | C | | |
| 20 (SUBSTRATE SOLUTION DISCHARGE 1) | O | O | O | O | O | C | C | C | C | C | C | C | C | C | C | O | O | C | C | O | O | |
| 21 (SUBSTRATE SOLUTION DISCHARGE 2) | O | O | O | O | O | C | C | C | C | C | C | C | C | C | C | O | C | O | C | C | O | O |
| 22 (MEASUREMENT LIQUID INTRODUCTION) | O | O | O | O | O | C | C | C | C | C | C | C | C | C | C | C | O | O | C | O | C | O |
| 23 (MEASUREMENT LIQUID CIRCULATION) | O | O | O | O | O | C | C | C | C | C | C | C | C | C | C | Open-Close | C | C | C | C | | |

Open: O
Close: C

According to the mix method of the present embodiment, partitioning and communicating of the first circulation flow path 10 are controlled by the opening and closing of the circulation flow path valves V1, V2, V3, and thereby, it is possible to determine the quantity of the first reagent, the analyte, and the second reagent and to mix the first reagent, the analyte, and the second reagent.

According to the capture method of the present embodiment, by mixing the liquid that includes a carrier particle in the first circulation flow path 10 which includes the capture part 40, the contact chance between the capture part 40 and the carrier particle is prompted, and it is possible to efficiently capture the carrier particle.

Further, by mixing the liquid that includes a carrier particle in the second circulation flow path 50 which includes the capture part 42, the contact chance between the capture part 42 and the carrier particle is prompted, and it is possible to efficiently capture the carrier particle.

According to the detection method of the present embodiment, pretreatment to detection can be continuously performed by one device, and a condition used for mixing of the pretreatment for detecting the sample substance and a condition used for detection can be independently selected in each circulation flow path by performing, as the pretreatment of detection, mixing of the first reagent, the analyte, and the second reagent and formation of the carrier particle-antigen-enzyme complex in a circulation flow path that is different from a circulation flow path in which detection of the antigen is performed. Thereby, the efficiency of mixing of liquid and detection of the sample substance is improved. Further, it is possible to prevent the antibody B which is adhered to a wall surface inside the circulation flow path 10 from being circulated in the second circulation flow path 50, and it is possible to reduce noise generation at the time of detection caused by the antibody B that does not form the carrier particle-antigen-enzyme complex.

[System]

A system in an embodiment of the present invention includes a control part that controls opening and closing of a valve in a circulation mixer. A system in an embodiment of the present invention includes a fluidic device and a control part that controls opening and closing of a valve of the fluidic device. The procedure of opening and closing of the valve is represented by the procedure indicated by the mix method using the circulation mixer 1a and the mix method, the capture method, and the detection method using the circulation mixer 1d.

According to the system of the present embodiment, as an example, it is possible to perform the mix method, the capture method, and the detection method in the circulation mixer.

As described above, according to the embodiment of the present invention, a circulation mixer capable of quantitatively determining the volume of each liquid mixed in the mixer accurately and capable of circulating liquid that includes a carrier particle and capturing the particle is provided. Further, the present invention provides a fluidic device that includes a circulation mixer. Further, the present invention provides a system that includes a control part that controls opening and closing of a valve in a circulation mixer. Further, the present invention provides a mix method, a capture method, and a detection method using a circulation mixer.

EXAMPLES

Next, Examples are shown, and the present invention is described further in detail. However, the present invention is not limited to the following Examples.

<Example 1> Capture of Magnetic Particle

Figure 12:
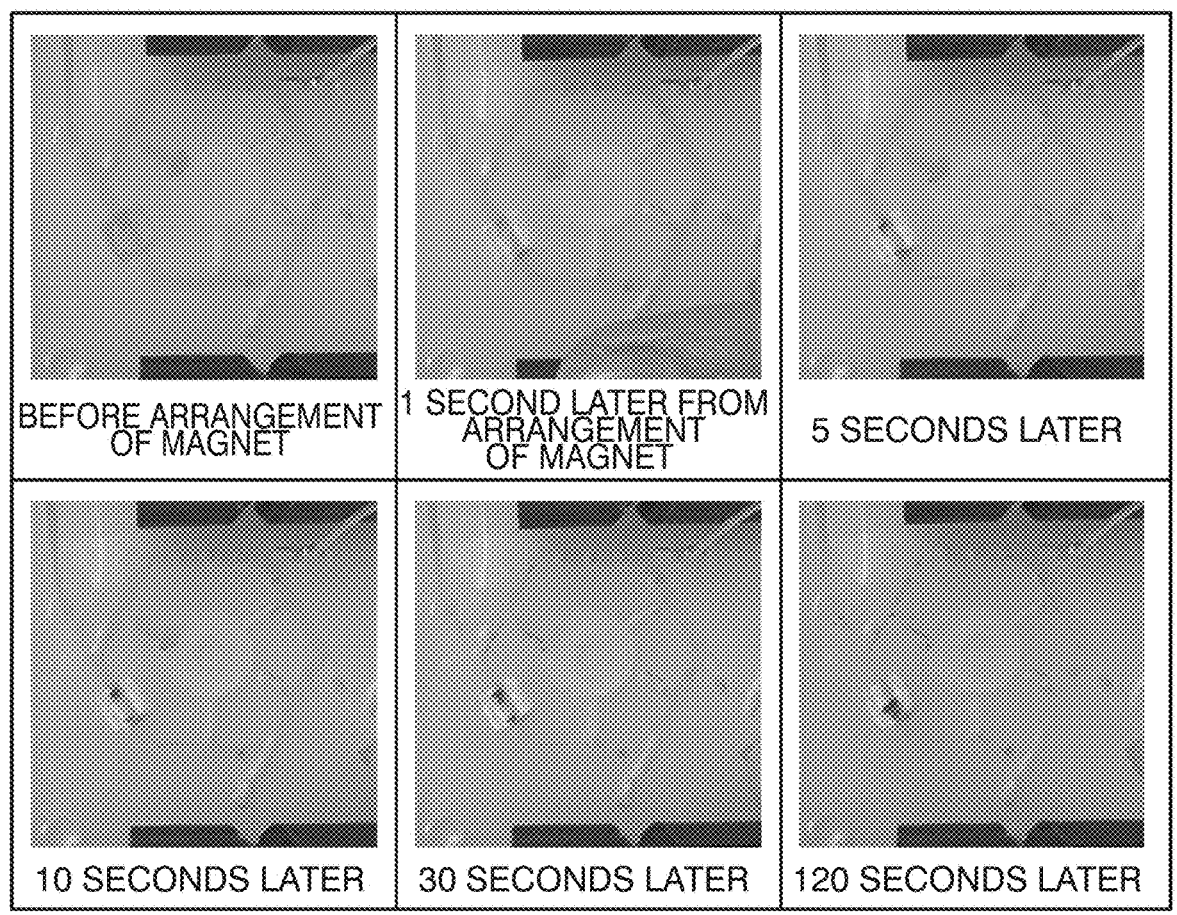
FIG. 12 is a view showing a result of capture of a magnetic particle in Example.

A fluidic device shown in FIG. 12 was fabricated. The fluidic device shown in FIG. 12 includes a circulation flow path, a capture part, a magnet arrangement part, an introduction flow path, and a pump valve arranged on the circulation flow path. It is possible to arrange a magnet at the magnet arrangement part.

As shown in FIG. 12, magnetic particle dispersion liquid was introduced from the introduction flow path to the circulation flow path, the pump valve was operated, and the magnetic particle dispersion liquid was circulated in the circulation flow path (before arranging the magnet). A magnet was arranged onto the magnet arrangement part while continuing circulation of the dispersion liquid, and a magnetic particle capture available state was obtained. FIG. 12 shows states of the fluidic device of 1 second later, 5 seconds later, 10 seconds later, 30 seconds later, and 120 seconds later from the arrangement of the magnet.

Figure 13:
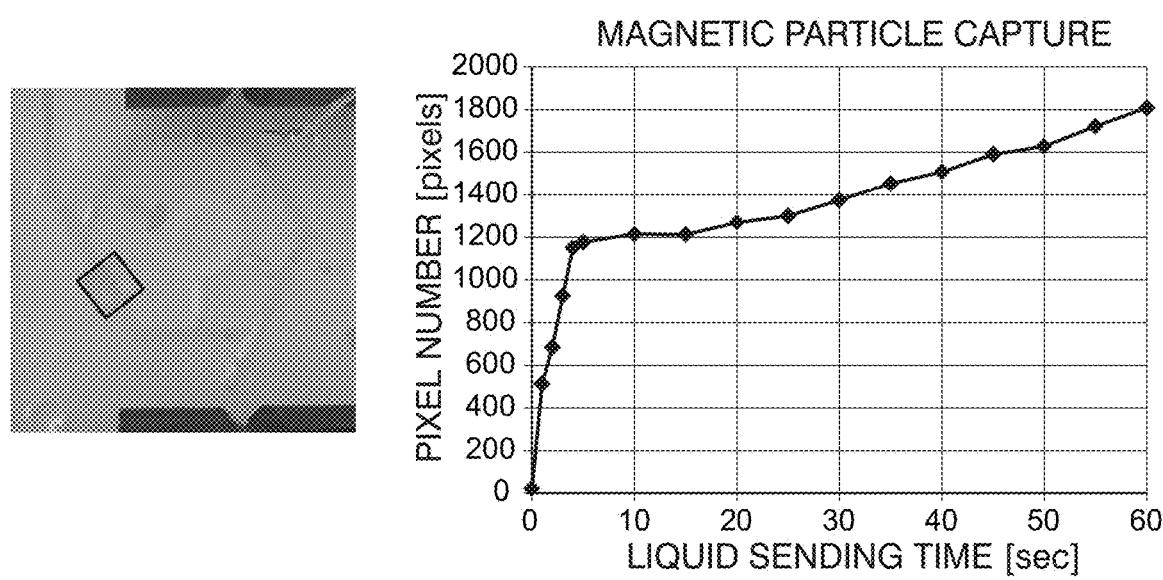
FIG. 13 is a view showing a result of capture of a magnetic particle in Example.

Further, the capture state of the magnetic particle at this time was quantitatively determined. An image of an area within a surrounding line that includes the capture part in the photograph shown in FIG. 13 was acquired, a histogram of 8 bit-gray value within the area was acquired by an image-processing apparatus, and the pixel number [pixel] having a threshold value of 130 or more was obtained. The result is shown in FIG. 13. The increase in the value of pixel number in accordance with the elapse of liquid sending time after arranging the magnet was confirmed, and it was shown that the capture amount of the magnetic particle in the capture part was gradually increased by the circulation of the magnetic particle dispersion liquid.

Thereby, it was clarified that by circulating the magnetic particle dispersion liquid, it was possible to improve the capture efficiency of the magnetic particle.

<Example 2> Redispersion of Magnetic Particle

Figure 14:
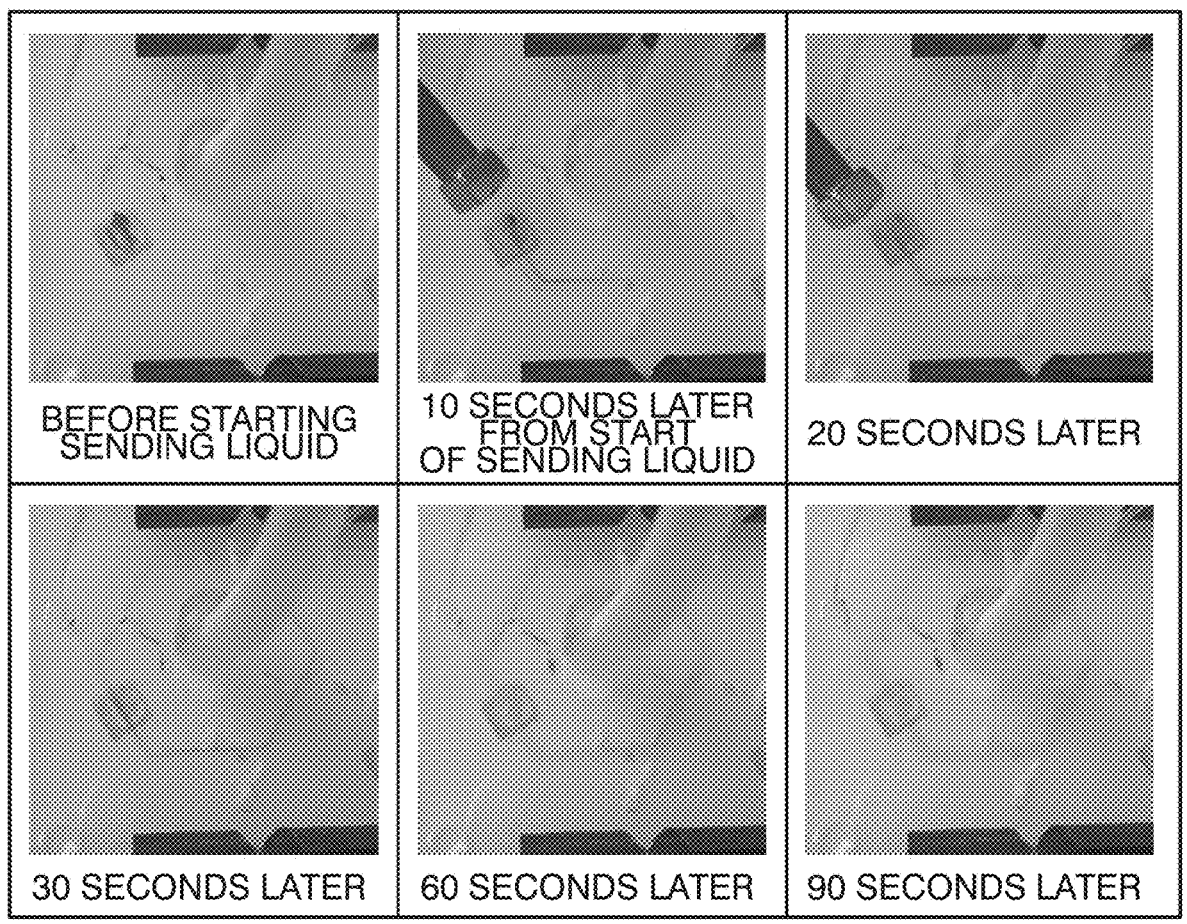
FIG. 14 is a view showing a result of redispersion of a magnetic particle in Example.

As shown in FIG. 14, liquid was discharged from the circulation flow path of the fluidic device in a state where the magnetic particle was captured in Example 1. Next, the magnet was removed from the magnet arrangement part of the capture part, and a release state in which the magnet was away from the circulation flow path was obtained (before starting sending liquid). Then, liquid that did not include the magnetic particle was sent to the circulation flow path. FIG. 14 shows states of the fluidic device of 10 seconds later, 20 seconds later, 30 seconds later, 60 seconds later, and 90 seconds later from the start of sending liquid.

Figure 15:
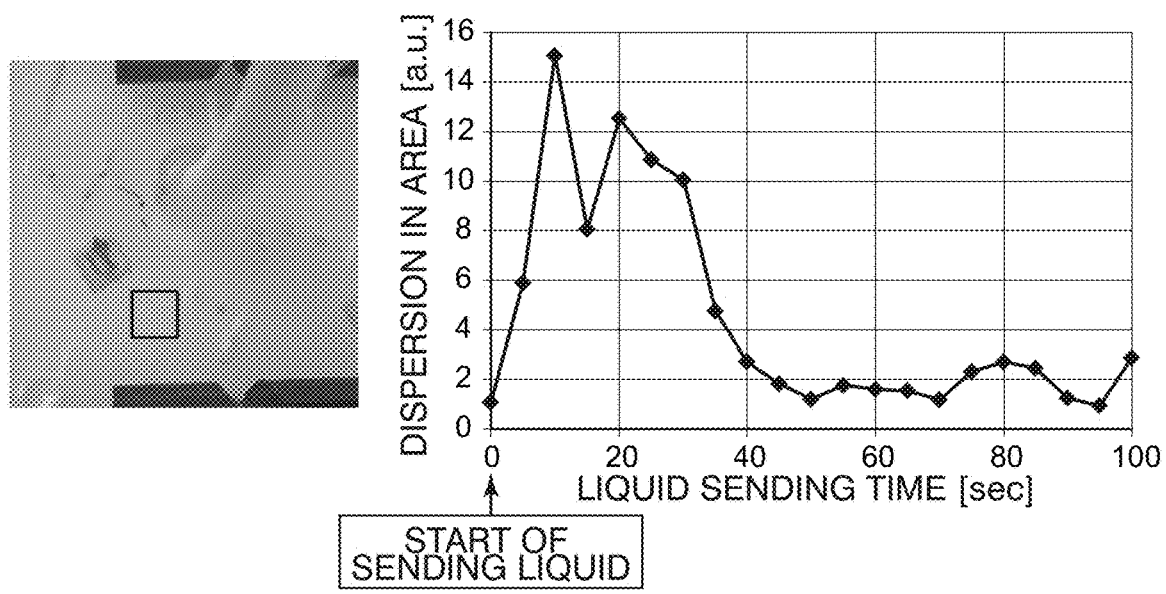
FIG. 15 is a view showing a result of redispersion of a magnetic particle in Example.

Further, the redispersion state of the magnetic particle at this time was quantitatively determined. An image of an area within a surrounding line that includes a flow path on the downstream of the capture part in the photograph shown in FIG. 15 was acquired, and the dispersion of luminance between the pixels in the area was calculated by an image-processing apparatus. The result is shown in FIG. 15. The increase in the value of dispersion in the area in accordance with the elapse of liquid sending time and the subsequent decrease were confirmed, and it was shown that the magnetic particle that was captured by the capture part was gradually dispersed in the liquid by the circulation of the magnetic particle dispersion liquid. Therefore, it was clarified that by circulating the liquid in the circulation flow path, it was possible to improve the redispersion efficiency of the magnetic particle.

<Example 3> Transport of Magnetic Particle

Figure 16:
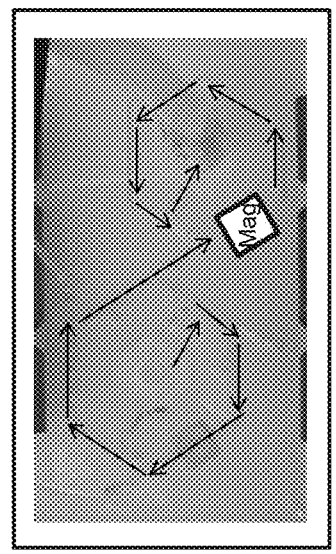
FIG. 16 is a view showing a result of transport and capture of a magnetic particle in Example.

A fluidic device shown in FIG. 16 was fabricated. The fluidic device shown in FIG. 16 includes a first circulation flow path, a capture part, a magnet arrangement part, an introduction flow path, and a pump valve arranged on the circulation flow path and includes a second circulation flow path, a capture part, a magnet arrangement part, and a pump valve arranged on the circulation flow path. It is possible to arrange a magnet at the magnet arrangement part. A connection flow path connects the circulation flow path and the second circulation flow path.

As shown in FIG. 16, magnetic particle dispersion liquid in the circulation flow path was introduced to the second circulation flow path via the connection flow path (during transport, after transport). In FIG. 16, the lower photograph after transport is a photograph showing a state in which the magnetic particle is captured in the capture part provided on the second circulation flow path. Therefore, it was shown that it was possible to transport the magnetic particle dispersion liquid from the first circulation flow path to the second circulation flow path. It is possible to introduce the magnetic particle from the first circulation flow path to the second circulation flow path, and therefore, the fluidic device shown in FIG. 16 is applicable, for example, to chemiluminescence detection or general electrochemical detection. Further, it is possible to capture the magnetic particle at the second circulation flow path, and therefore, the fluidic device shown in FIG. 16 is applicable, for example, to an analysis method of a sample substance such as fluorescence detection on the magnetic particle and electrochemical detection associated with insolubilization reaction (for example, deposition of silver) in which a soluble substance such as a metal ion is converted into an insoluble substance.

The configurations in the embodiments, the combination of the configurations, and the like are examples. Addition, omission, and substitution of the configuration and other changes can be made without departing from the scope of the invention. The invention is not limited by the embodiments and is limited only by claims.

What is claimed is:

1. A fluidic device, comprising:
a circulation looped flow path; and
a capture part arranged on the circulation looped flow path and configured to capture a sample substance in a solution and/or a detection part arranged on the circulation looped flow path and configured to detect a sample substance in a solution, wherein
the circulation looped flow path has two or more circulation looped flow path valves, each of the circulation looped flow path valves partitioning the circulation looped flow path into a first partition and a second partition;
a first introduction flow path is directly connected to the first partition of the circulation looped flow path;
a second introduction flow path is directly connected to the second partition of the circulation looped flow path;
a discharge flow path is connected to the circulation looped flow path;
the first introduction flow path has a first introduction flow path valve;
the second introduction flow path has a second introduction flow path valve; and
the discharge flow path has a discharge flow path valve.

2. The fluidic device according to claim 1, wherein
the capture part captures a sample substance that is bound to a carrier particle or the detection part detects a sample substance that is bound to a carrier particle.

3. The fluidic device according to claim 2, wherein
the capture part is configured such that an affinity with respect to the carrier particle is controllable.

4. The fluidic device according to claim 2, wherein
a magnetic bead or a magnetic particle is used for the carrier particle, and
a magnet may be arranged in the vicinity of the capture part outside a flow path of the circulation looped flow path.

5. The fluidic device according to claim 1, wherein
volumes of a plurality of solutions are quantitatively determined in the circulation looped flow path, and the quantitatively determined solutions are capable of being circulated and mixed.

6. The fluidic device according to claim 1, wherein
the first introduction flow path, the second introduction flow path, and the discharge flow path are configured such that a different solution is capable of being introduced to each of the partitions of the circulation looped flow path.

7. The fluidic device according to claim 1, wherein
at least one of the introduction flow path and the discharge flow path is arranged in the vicinity of the circulation looped flow path valve.

8. The fluidic device according to claim 1, wherein the circulation looped flow path has a pump by which a solution is circulated.

9. The fluidic device according to claim 8, wherein the pump includes at least three pump valves arranged on the circulation looped flow path.

10. The fluidic device according to claim 9, wherein at least one of the circulation looped flow path valves is used for the pump valve.

11. The fluidic device according to claim 1, wherein the capture part and the detection part are arranged at the same position of the circulation looped flow path.

12. The fluidic device according to claim 1, further comprising:
at least one other circulation looped flow path on which a detection part that detects a sample substance in a solution is arranged, wherein
the circulation looped flow paths are connected to each other by a connection flow path.

13. A system, comprising:
a fluidic device according to claim 1; and a control part configured to control opening and closing of a valve.

* * * * *